US011771752B2

(12) United States Patent
Singh

(10) Patent No.: US 11,771,752 B2
(45) Date of Patent: Oct. 3, 2023

(54) COMPOSITION FOR ORAL OR NASAL DELIVERY OF TETANUS, DIPHTHERIA, AND PERTUSSIS VACCINE ALONE OR IN COMBINATION USING NEUROTOXIN ASSOCIATED PROTEINS

(71) Applicant: Prime Bio, Inc., North Dartmouth, MA (US)

(72) Inventor: Bal Ram Singh, North Dartmouth, MA (US)

(73) Assignee: Prime Bio, Inc., Dartmouth, MA (US)

( * ) Notice: Subject to any disclaimer, the term of this patent is extended or adjusted under 35 U.S.C. 154(b) by 45 days.

(21) Appl. No.: 15/064,651

(22) Filed: Mar. 9, 2016

(65) Prior Publication Data

US 2019/0076518 A1    Mar. 14, 2019

(51) Int. Cl.
*A61K 39/02* (2006.01)
*A61K 39/08* (2006.01)
*A61K 39/00* (2006.01)
*C12N 15/70* (2006.01)
*C12N 15/62* (2006.01)
*A61P 31/04* (2006.01)
*C07K 14/19* (2006.01)
*C07K 14/34* (2006.01)
*C07K 14/33* (2006.01)
*C07K 14/235* (2006.01)
*A61K 39/395* (2006.01)
*C12N 15/66* (2006.01)

(52) U.S. Cl.
CPC ........ *A61K 39/099* (2013.01); *A61K 39/0018* (2013.01); *A61K 39/08* (2013.01); *A61K 39/39525* (2013.01); *A61P 31/04* (2018.01); *C07K 14/19* (2013.01); *C07K 14/235* (2013.01); *C07K 14/33* (2013.01); *C07K 14/34* (2013.01); *C12N 15/62* (2013.01); *C12N 15/66* (2013.01); *C12N 15/70* (2013.01); *A61K 2039/542* (2013.01); *A61K 2039/6031* (2013.01); *A61K 2039/622* (2013.01)

(58) Field of Classification Search
None
See application file for complete search history.

(56) References Cited

PUBLICATIONS

Lam et al (Curr Opin. Struct. Biol, 31:89-95, 2015).*

* cited by examiner

*Primary Examiner* — Brian Gangle

(57) ABSTRACT

The present invention describes a neurotoxin associated protein from botulinum neurotoxin complex used as an oral or nasal delivery system for a vaccine. The vaccine is selected from tetanus, diphtheria and pertussis alone or in combination. Further the oral or nasal delivery of tetanus vaccine in combination with other drug molecules.

13 Claims, 14 Drawing Sheets

Specification includes a Sequence Listing.

Fig. 5A

```
TCACTAATTCTGTTCATGACCCATTAATAAAATCCACCAAAATATATTCATATTTTCCAT 1800
CTGTAATCAGTAAAGTTAACCAAGGTGCACAAGGAATTTTATTCTTACAGTGGGTGAGAG 1860
CTGTAATCAGTAAAGTTAACCAAGGTGCACAAGGAATTTTATTCTTACAGTGGGTGAGAG 1852
ATATAATTGATGATTTTACCAATGAAATCTTCACAAAAAACTACTATTGATAAAATTTCAG 1920
ATGTATCCACTATTGTTCCTTATATAGGACCCGCATTAAACATTGTAAAACAAGGCTATG 1980
AGGGAAACTTTATAGGCGCTTTAGAAACTACCGGAGTGGTTTTATTATTAGAATATATTC 2040
CACAAATTACTTTACCAGTAATTGCAGCTTTATCTATAGCAGAAAGTAGCACACAAAAAG 2100
AAAAGATAATAAAAACAATAGATAACTTTTTAGAAAAAAGATATGAAAAATGGATTGAAG 2160
TATATAAACTAGTAAAAGCAAAATGGTTAGCCACAGTTAATACGCAATTCCAAAAAAGAA 2220
GTTATCAAATGTATAGATCTTTAGAATATCAAGTACATGCAATAAAAAAAATAATAGACT 2280
ATGAATATAAAATATATTCAGGACCTCATAAGGAACAAATTGCCGACGAAATTAATAATC 2340
TGAAAAACAAACTTGAAGAAAAGGCTAATAAAGCAATGATAAACATAAATATATTTATGA 2400
GGGAAAGTTCTAGATCATTTTAGTTAATCAAATGATTAACGAAGCTAAAAAGCAGTTAT 2460
TAGAGTTTGATACTCAAAGCAAAAATATTTTAATGCAGTATATAAAAGCAAATTCTAAAT 2520
TTATAGGTATAACTGAACTAAAAAAATTAGAATCAAAAATAAACAAAGTTTTTTCAACAC 2580
CAATTCCATTTTCTTATTCTAAAAATCTGGATTGTTGGGTTGATAATGAAGAAGATATAG 2640
ATGTTATATTAAAAAAGAGTACAAATTTTAAATTTAGATATTAATAATGATATTATATCAG 2700
ATATATCTGGGTTTAATTCATCTGTAATAACATATCCAGATGCTCAATTGGTGCCCGGAA 2760
TAAATGGCAAAGCAATAGATTTAGTAAACAATGAATCTTCTGAAGTTATAGTGCATAAAG 2820
CTATGGATATTGAATATAATGATATGTTTAATAATTTTACCGTTAGCTTTTGGTTGAGGG 2880
TTCCTAAAGTATCTGCTAGTCATTTAGAAGAATATGGCACAAATGAGTATTCAATAATTA 2940
GCTCTATGAAAAAATATAGTCTATCAATAGGATCTGGTTGGAGTGTATCACTTAAAGGTA 3000
ATAACTTAATATGGACTTTAAAAGATTCCGCCGGAGAAGTTAGACAAATAACTTTTACCG 3060
ATTTATCTGATAAATTTAATGCTTATTTAGCAAATAAATGGGTTTTATAACTATTACTA 3120
ATGATAGATTATCTTCTGCTAATTGTATATAAATGGAGTACTTATGGGAAGTGCAGAAA 3180
TTACTGGTTTACGAGCTATTAGAGAGGATAATAATATAACATTAAAACTAGATAGATGTA 3240
ATAATAATAATCAATACGTTTCTATTGATAAATTTAGGATATTTTGCAAAGCATTAAATC 3300
CAAAGAGATTGAAAAATTATACACAAGTTATTTATCTATAACCTTTTTAAGAGACTTCT 3360
GGGGAAACCCTTTACGATATGATACAGAATATTATTTAATACCAGTAGCTTCTAGTTCTA 3420
AAGATGTTCAATTGAAAAATATAAACAGATTATATGTATTTCACAAATGCGCCATCGTATA 3480
CTAACGGAAAATTGAATATATATTATAGAAGGTTATATAATGACTAAAAATTTATTATAA 3540
AAAGATATAGACCTAATAATGAAATAGATTGTTTTGTTAAATCAAGTGATTTATTAAAT 3600
```

Fig. 5B

```
TATATGTATCATATAACAATAATGAGCACATTGTAGGTTATCCGAAAGATGGAAATGCCT 3660
TTAATAATCTTGATAGAATTCTAAGAGTAGGTTATAATGCCCCAGTATCCCTCTTTATA 3720
AAAAAATGGAAGCAGTAAAATTGCGTGATTTAAAAACCTATTCTGTACAACTTAAATTAT 3780
ATGATGATAAAAATGCATCTTTAGGACTAGTAGGTACCCATAATGGTCAAATAGGCAACG 3840
ATCCAAATAGGGATATATTAATTGCAAGCAACTGGTACTTTAATCATTTAAAAGATAAAA 3900
TTTTAGGATGTGATTGGTACTTTGTACCTACAGATGAAGGATGGACAAATGAT CATCACC 3960      6X His
ATCACCATCAC TAA GGCCTGCAGCCAAGCTTAATTAGCTGAGCTTGGACTCCTGTTGATA 4020
GATCCAGTAATGACCTCAGAACTCCATCTGGATTTGTTCAGAACGCTCGGTTGCCGCCGG 4080
GCGTTTTTTATTGGTGAGAATCCAAGCTAGCTTGGCGAGATTTTCAGGAGCTAAGGAAGC 4140
TAAAATGGAGAAAAAAATCACTGGATATACCACCGTTGATATATCCCAATGGCATCGTAA 4200
AGAACATTTTGAGGCATTTCAGTCAGTTGCTCAATGTACCTATAACCAGACCGTTCAGCT 4260
GGATATTACGGCCTTTTTAAAGACCGTAAAGAAAAATAAGCACAAGTTTTATCCGGCCTT 4320
TATTCACATTCTTGCCCGCCTGATGAATGCTCATCCGGAATTTCGTATGGCAATGAAAGA 4380
CCGTGAGCTGGTGATATGGGATAGTGTTCACCCTTGTTACACCGTTTTCCATGAGCAAAC 4440
TGAAACGTTTTCATCGCTCTGGAGTGAATACCACGACGATTTCCGGCAGTTTCTACACAT 4500
ATATTCGC 4508
```

Fig. 5C

AA Sequence within Dr TaIx, Reference and QI23911( from Genebank)

```
DrTaIX     IGMPITIKNFRYSDPVRNDTIIMMEPPYCKGLDIYYKAFKITDRIWIVPERYEFGTKPED    60
Reference  --MPITIKNFRYSDPVRNDTIIMMEPPYCKGLDIYYKAFKITDRIWIVPERYEFGTKPED    58
CN3911     --MPITIKNFRYSDPVRNDTIIMMEPPYCKGLDIYYKAFKITDRIWIVPERYEFGTKPED    58
             ************************************************************

DrTaIX     FNPPSSLIEGASEYYDPNYLRIDSDKDRFLQTMVKLFNRIKNNVAGEALLNKIDNAIPYL   120
Reference  FNPPSSLIEGASEYYDPNYLRIDSDKDRFLQTMVKLFNRIKNNVAGEALLDKIDNAIPYL   118
CN3911     FNPPSSLIEGASEYYDPNYLRIDSDKDRFLQTMVKLFNRIKNNVAGEALLDKIDNAIPYL   118
             ********************************************* **************

DrTaIX     GNSYSLLDKFDTNSNSVSFNLLEQDPSGATTKSAMLTNLIIFGPGPVLNKQEVRGIVLRV   180
Reference  GNSYSLLDKFDTNSNSVSFNLLEQDPSGATTKSAMLTNLIIFGPGPVLNKQEVRGIVLRV   178
CN3911     GNSYSLLDKFDTNSNSVSFNLLEQDPSGATTKSAMLTNLIIFGPGPVLNKQEVRGIVLRV   178
             ************************************************************

DrTaIX     DNKNYFPCRDGFGSIMQMAFCPEYVPTFDNVIENITSLTIGKSKYFCDPALLLMGH A LIHV   240
Reference  DNKNYFPCRDGFGSIMQMAFCPEYVPTFDNVIENITSLTIGKSKYFCDPALLLMGH E LIHV   238
CN3911     DNKNYFPCRDGFGSIMQMAFCPEYVPTFDNVIENITSLTIGKSKYFCDPALLLMGH E LIHV   238
             ***************************************************    ****

DrTaIX     LHGLYGMQVSSHEIIPSKQEIYMQHTYPISAE A LFTFGGQDANLISIDIKNDLYEKTLND   300
Reference  LHGLYGMQVSSHEIIPSKQEIYMQHTYPISAE E LFTFGGQDANLISIDIKNDLYEKTLND   298
CN3911     LHGLYGMQVSSHEIIPSKQEIYMQHTYPISAE E LFTFGGQDANLISIDIKNDLYEKTLND   298
             ********************************   *************************

DrTaIX     YKAIRNKLSQVTSQNDPNIDIDSYKQIYQCKYQFDKDSNGQYIVNEDKFQILYNSDMYGF   360
Reference  YKAIRNKLSQVTSQNDPNIDIDSYKQIYQCKYQFDKDSNGQYIVNEDKFQILYNSDMYGF   358
CN3911     YKAIRNKLSQVTSQNDPNIDIDSYKQIYQCKYQFDKDSNGQYIVNEDKFQILYNSDMYGF   358
             ************************************************************

DrTaIX     TEIELGKKFNIKTRLSYFSNGHDPVKIPNLLDDTIYNDTEGFNIESKDLKSEYKGQDMRV   420
Reference  TEIELGKKFNIKTRLSYFSNGHDPVKIPNLLDDTIYNDTEGFNIESKDLKSEYKGQDMRV   418
CN3911     TEIELGKKFNIKTRLSYFSNGHDPVKIPNLLDDTIYNDTEGFNIESKDLKSEYKGQDMRV   418
             ************************************************************

DrTaIX     NTNQAFRNVDGSGLVSKLIGLCKKIIPPTNIRENLYNRTASLTDLGGELCIKKNEDLTFI   480
Reference  NTNQAFRNVDGSGLVSKLIGLCKKIIPPTNIRENLYNRTASLTDLGGELCIKKNEDLTFI   478
CN3911     NTNQAFRNVDGSGLVSKLIGLCKKIIPPTNIRENLYNRTASLTDLGGELCIKKNEDLTFI   478
             ************************************************************

DrTaIX     AEKNSFSEEPFQDEIVSYNTKNKPLNFNYSLDKII L DYNLQSKITLPNDRITPVTKGIPY   540
Reference  AEKNSFSEEPFQDEIVSYNTKNKPLNFNYSLDKII L DYNLQSKITLPNDRITPVTKGIPY   538
CN3911     AEKNSFSEEPFQDEIVSYNTKNKPLNFNYSLDKII V DYNLQSKITLPNDRITPVTKGIPY   538
             **********************************   ************************

DrTaIX     APEYKSNAASTIEIHNIDDNTIYQYLYACKSPTTLCRITMNHSVDDALINSTKIYSYFPS   600
Reference  APEYKSNAASTIEIHNIDDNTIYQYLYACKSPTTLCRITMNHSVDDALINSTKIYSYFPS   598
CN3911     APEYKSNAASTIEIHNIDDNTIYQYLYACKSPTTLCRITMNHSVDDALINSTKIYSYFPS   598
             ************************************************************

DrTaIX     VISKVNQGAQGILFLQWVRDIIDDFTNESSQKTTIDKISDVSTIVPYIGPALNIVKQGYE   660
Reference  VISKVNQGAQGILFLQWVRDIIDDFTNESSQKTTIDKISDVSTIVPYIGPALNIVKQGYE   658
CN3911     VISKVNQGAQGILFLQWVRDIIDDFTNESSQKTTIDKISDVSTIVPYIGPALNIVKQGYE   658
             ************************************************************

DrTaIX     GNFIGALETTGVVLLLEYIPEITLPVIAALSIAESSTCKEKIIKTIDNFLEKRYEKWIEV   720
Reference  GNFIGALETTGVVLLLEYIPEITLPVIAALSIAESSTCKEKIIKTIDNFLEKRYEKWIEV   718
CN3911     GNFIGALETTGVVLLLEYIPEITLPVIAALSIAESSTCKEKIIKTIDNFLEKRYEKWIEV   718
             ************************************************************
```

Fig.6A

```
OxTeIX       YKLVKAKWLGTVNTQFQKRSYQMYRSLEYQVDAIKKIIDYEYKIYSGPDKEQIADEIKIL    780
Reference    YKLVKAKWLGTVNTQFQKRSYQMYRSLEYQVDAIKKIIDYEYKIYSGPDKEQIADEIKIL    778
CN3911       YKLVKAKWLGTVNTQFQKRSYQMYRSLEYQVDAIKKIIDYEYKIYSGPDKEQIADEIKIL    778
             ************************************************************

OxTeIX       KNKLEEKANKAMINIIFMRESSRSFLVNKMINEAKKQLLEFDTQSKNILMQYIKANSKF     840
Reference    KNKLEEKANKAMINIIFMRESSRSFLVNKMINEAKKQLLEFDTQSKNILMQYIKANSKF     838
CN3911       KNKLEEKANKAMINIIFMRESSRSFLVNKMINEAKKQLLEFDTQSKNILMQYIKANSKF     838
             **********************************************************

OxTeIX       IGITELKKLESKINKVFSTPIPFSYSKNLDCWVDNEEDIDVILKKSTILNLDINNDIISD    900
Reference    IGITELKKLESKINKVFSTPIPFSYSKNLDCWVDNEEDIDVILKKSTILNLDINNDIISD    898
CN3911       IGITELKKLESKINKVFSTPIPFSYSKNLDCWVDNEEDIDVILKKSTILNLDINNDIISD    898
             ************************************************************

OxTeIX       ISGFNSSVITYPDAQLVPGINGKAIHLVNQESSEVIVHKAMDIEVNDMFNNFTVSFWLRV    960
Reference    ISGFNSSVITYPDAQLVPGINGKAIHLVNQESSEVIVHKAMDIEVNDMFNNFTVSFWLRV    958
CN3911       ISGFNSSVITYPDAQLVPGINGKAIHLVNQESSEVIVHKAMDIEVNDMFNNFTVSFWLRV    958
             ************************************************************

OxTeIX       PKVSASHLEQYGTNEYSIISSMKK Y SLSIGSGWSVSLKGNNLIWTLKDSAGEVRQITFRD 1020
Reference    PKVSASHLEQYGTNEYSIISSMKK Y SLSIGSGWSVSLKGNNLIWTLKDSAGEVRQITFRD 1018
CN3911       PKVSASHLEQYGTNEYSIISSMKK H SLSIGSGWSVSLKGNNLIWTLKDSAGEVRQITFRD 1018
             ************************ ************************************

OxTeIX       L S DKFNAYLANKWVFITITNDRLSSANLYINGVIMGSAEITGLGAIREDKNITLKLDRCN 1080
Reference    L S DKFNAYLANKWVFITITNDRLSSANLYINGVIMGSAEITGLGAIREDKNITLKLDRCN 1078
CN3911       L P DKFNAYLANKWVFITITNDRLSSANLYINGVIMGSAEITGLGAIREDKNITLKLDRCN 1078
             * ***********************************************************

OxTeIX       NNNQYVSIDKFRIFCKALNPKEIEKLYTSYLSITFLRDFWGNPLRYDTEYYLIFVASSSK  1140
Reference    NNNQYVSIDKFRIFCKALNPKEIEKLYTSYLSITFLRDFWGNPLRYDTEYYLIFVASSSK  1138
CN3911       NNNQYVSIDKFRIFCKALNPKEIEKLYTSYLSITFLRDFWGNPLRYDTEYYLIFVASSSK  1138
             ***********************************************************

OxTeIX       DVQLKNITDWMYLTNAPSYTNGKLNIYYRRLYNGLKFIIKRYTPNNEIDSFVKS X DFIKL 1200
Reference    DVQLKNITDWMYLTNAPSYTNGKLNIYYRRLYNGLKFIIKRYTPNNEIDSFVKS X DFIKL 1198
CN3911       DVQLKNITDWMYLTNAPSYTNGKLNIYYRRLYNGLKFIIKRYTPNNEIDSFVKS G DFIKL 1198
             ****************************************************** *****

OxTeIX       YVSYNNIEHIVGYPKDGNAFNNLDRILRVGYNAPGIPLYKMEAVKLRDLKTYSVGLKLY   1260
Reference    YVSYNNIEHIVGYPKDGNAFNNLDRILRVGYNAPGIPLYKMEAVKLRDLKTYSVGLKLY   1258
CN3911       YVSYNNIEHIVGYPKDGNAFNNLDRILRVGYNAPGIPLYKMEAVKLRDLKTYSVGLKLY   1258
             **********************************************************

OxTeIX       DDKNASLGLVGTHNGQIGNDPNRDILIASNWYFNGNLKDKILGCDWYFVPTDEGWTNDNN  1320
Reference    DDKNASLGLVGTHNGQIGNDPNRDILIASNWYFNGNLKDKILGCDWYFVPTDEGWTND---  1315
CN3911       DDKNASLGLVGTHNGQIGNDPNRDILIASNWYFNGNLKDKILGCDWYFVPTDEGWTND---  1315
             *********************************************************

OxTeIX       NNH-GLQPSLIS-ANTFVDRSSNDLRTPSGFVQNARLPPGVFYN-ESKLAWRDFQELRKL 1377
Reference    ------------------------------------------------------------
CN3911       ------------------------------------------------------------
```

COMPOSITION FOR ORAL OR NASAL DELIVERY OF TETANUS, DIPHTHERIA, AND PERTUSSIS VACCINE ALONE OR IN COMBINATION USING NEUROTOXIN ASSOCIATED PROTEINS

TECHNICAL FIELD

This invention relates to a composition vaccine in combination with neurotoxin associated proteins for oral or nasal delivery of the vaccine. Moreover, the present invention particularly relates to oral delivery of tetanus vaccine with the help of proteins known as neurotoxin associated proteins (NAPs) from *Clostridium botulinum*. The NAPs combine with vaccine candidates made of domains of tetanus neurotoxin or detoxified recombinant tetanus neurotoxin (Dr-TeNT) for the delivery of the tetanus vaccines by oral or nasal passage.

BACKGROUND OF THE INVENTION

Botulinum neurotoxins (BoNT), is one of the most toxic substance known to man, is produced by *Clostridium botulinum*. The clostridial neurotoxin family comprises seven BoNT serotypes (A-G), produced mainly by as a complex with a group of neurotoxin-associated proteins (NAPs). The botulinum neurotoxin complex is the only known example of a protein complex where a group of proteins (NAPs) protect another protein (BoNT) against acidity and proteases of the GI tract. The clostridial neurotoxin family comprises seven BoNT serotypes (A-G), produced mainly by *Clostridium botulinum* and the tetanus neurotoxin (TeNT), produced by *Clostridium tetani*. Although the BoNTs and TeNT function via a similar initial physiological mechanism of action, producing paralysis by inhibition of neurotransmission. BoNTs are synthesized as a single polypeptide chain comprising several domains with distinct functions that contribute to the mechanism of toxicity. Other proteins produced from *Clostridium botulinum* form a complex with BoNT that may contribute to toxicity and the stability of the BoNT in the natural environment of food poisoning. These proteins are known as Neurotoxin Associated Proteins (NAPs). When pure BoNT is exposed to the digestive conditions with acidic fluid and proteases, BoNT degrade into inactive small peptides. Thus the pure BoNT exerts no oral toxicity. The toxicity exerts only when the BoNT is associated with NAPs, which protect BoNT against acidity and proteases of the GI tract. The NAPs not only protect BoNTs from the acidity and proteases of the GI tract but also assist in translocation of BoNT across the gut wall.

Tetanus is often a fatal disease caused by tetanus neurotoxin (TeNT) produced by *Clostridium tetani*, same family of *Clostridium botulinum*, which can infect wounds resulting from general cuts, needle use, unhygienic birth practices. Tetanus is a disease that is entirely preventable with immunization of the population with tetanus toxoid vaccine. The tetanus toxoid vaccine is readily available at health clinics. The tetanus vaccination has become common throughout the world at least during infant ages. Later, booster shots are recommended for whole population every 10 years.

One hundred percent tetanus immunization is needed for the world population, as this is a disease, which often turns fatal. In addition, there is a need for booster shots of tetanus every 10 years, which frequently is overlooked. Current delivery system for tetanus vaccine involves needle injection, which is inconvenient and frightening for many people, especially to children. Currently there are over 200,000 annual tetanus deaths (mostly maternal and neonatal) worldwide which could be prevented with effective immunization. Therefore, tetanus vaccine is an ideal system for the development of an oral or intranasal delivery system.

There is a great need for child vaccination by developing a needle free immunization systems for a much needed tetanus vaccination. Currently most vaccines are still injected into body by needles. It is stressful and painful, especially to young children whom get most of their vaccines at early ages. Oral delivery method proposed for administration of tetanus vaccine will be less painful, and safer. There will be no issue of contaminated needles.

Further, currently many vaccines cannot be delivered by oral route because the harsh digestive conditions in stomach like very low pH and bile acid, and proteases. Moreover, currently there are several safety concerns related to the injection of vaccines, e.g., allergic reaction, and contaminated antigen.

The TeNT, having over 35% sequence homology with BoNTs, and sharing much of the structural and functional features of BoNT, but is not a food poison due to the lack of NAPs. NAPs from one serotype of BoNT binding and protecting another serotype of BoNT, therefore NAPs can also bind, protect and translocate vaccines across the gut wall, specially TeNT or TeNT vaccine due to sequence homology.

Therefore the present invention uses NAPs of botulinum neurotoxin for oral and intranasal delivery of vaccines, specially tetanus vaccine.

At present tetanus vaccine is prepared by treating tetanus toxin with formaldehyde, trace amount of formaldehyde is left in the vaccine to prevent possible reversion. Formaldehyde causes adverse effect upon injection.

Further, currently tetanus vaccination is recommended every 10 years, most of the adult population is not up to date on tetanus vaccination due to the difficulties associated with administration of the vaccination.

Formalin-inactivated Tetanus toxoid is currently used for the immunization. It is recommended to give three to four doses in the childhood and booster dose to adult every 10 years. Tetanus toxoid is available in combination with Diphtheria and Pertussis. The present mode of administration of the Formalin-inactivated Tetanus toxoid is alone or in combination with Diphtheria and Pertussis as intramuscular injection. On the intramuscular injection local reactions consisting of pain, erythema, tenderness and induration at the injection site are common and may be associated with systemic reactions including transient fever and irritability. The reactions are basically due to the formalin present in the formulation. Thus, there is a continual need to develop oral tetanus vaccine alone or in combination with diphtheria and pertussis.

Availability of an oral delivery system would facilitate the vaccination schemes for pregnant women, infants and the world population in general. Currently no such vaccine delivery system is available, nor there is any effort known to be underway in this direction.

The present invention can solve the problem of harsh digestive conditions in stomach like very low pH and bile acid, and proteases by using NAPs as adjuvants to protect the recombinant protein vaccines to go through this harsh condition. Further, with the present invention, NAPs protect heavy chain of tetanus toxoid or recombinant detoxified tetanus neurotoxin from intestinal enzymes and facilitates the vaccine to evoke the immune response.

Further, the present invention solves the problem of safety concerns related to the injection of vaccines by not requiring an injection.

Further, the present invention solves the problem of introduction of formaldehyde. The present invention will eliminate the possibility of the introduction of formaldehyde to the patient both due to the novel method of preparation of the vaccine and delivery system.

Further, the present invention will solve the problems associated with the recommended administering of an injection, because the present invention is an oral/intranasal vaccination, and it will allow mass vaccination by untrained workers, or even self-vaccination.

Further, the present invention will solve the problem associated with the rapid release of the vaccine. Because present invention delivered as an oral or intranasal vaccine, it will have a slower release rate compared to injection.

Further, the present invention will solve the above mentioned problems related to injections. The present invention is an oral vaccine, where NAPs as well as the mucous in the digestion system will provide possible protection against the above mentioned safety issues.

Further, NAPs in the vaccine formulation will increase the bioavailability of the vaccine when administered orally or intranasally.

BRIEF DESCRIPTION OF THE DRAWINGS

FIG. 5A-5C shows Nucleotide sequence of DrTeNT (3951 bp, including stop codon), which encodes for the full length double mutant tetanus gene. This sequence is submitted as Sequence ID No.3

FIG. 6A-6B shows Amino acid sequence alignment of DrTeNT (This sequence is submitted as Sequence ID No.1), reference (data from wildtype genomic DNA) this sequence is submitted as Sequence ID No.2, and CN3911 from Genebank.

FIG. 10. SDS-PAGE analysis of DrTeNT, NAPs, DrTeNT+NAPs load to the G-100 column, and DrTeNT+NAPs elution pool from the G-100 gel filtration column.

OBJECT OF THE INVENTION

Figure 1:
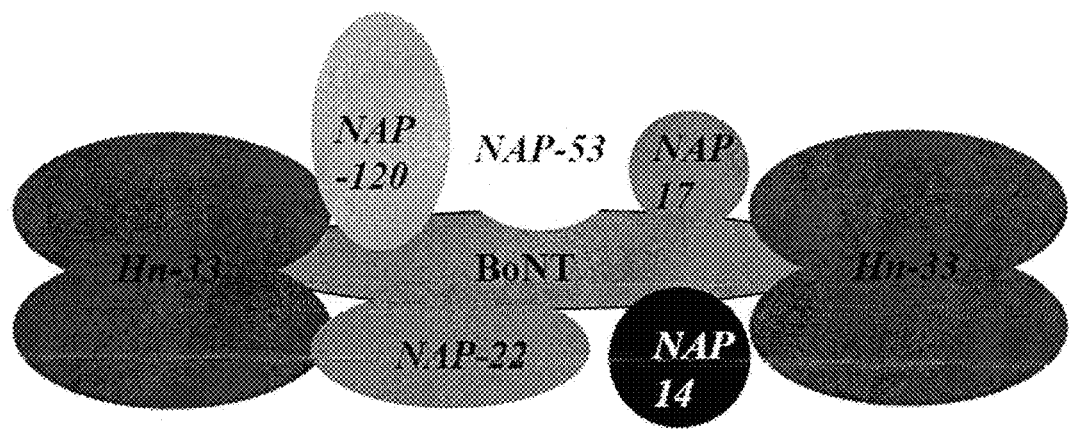
FIG. 1 shows a diagram of botulinum neurotoxin and its associated proteins.

Main object of the present invention is to provide a novel composition for the delivery of vaccine by oral or nasal administration.

Another object of present invention is to provide a novel composition for oral or nasal delivery of tetanus vaccine.

Yet another objective of present invention is to provide a novel composition for oral or nasal delivery of Tetanus, Diphtheria, and Pertussis Vaccine either alone or in combination thereof.

Another object of present invention is the use of neurotoxin associated protein (NAPs) for the oral or nasal delivery of the vaccine.

Another object of the present invention is the use of neurotoxin associated protein (NAPs) of *Clostridium botulinum*.

Yet another object of present invention is to provide a process for preparation of NAPs from type A *Clostridium botulinum*.

Yet another objective of present invention is to provide a process for the preparation of tetanus toxoid vaccine.

Yet another object of the present invention is to provide a process for the preparation of tetanus toxoid vaccine.

Yet another object of present invention is to provide first and second generation process for the preparation of tetanus toxoid vaccine.

Yet another object of present invention is to provide a process for the third generation tetanus vaccine as Detoxified recombinant tetanus neurotoxin (DrTeNT). DrTeNT amino acid sequence is submitted as Sequence ID No.1

Yet another object of present invention is to provide a testing model for the effectiveness of the oral and intranasal delivery of the vaccine.

Yet another object of present invention is to provide a testing model in rabbit or another suitable model for the effectiveness of the oral and intranasal delivery of the vaccine.

Another object of the present invention is oral or nasal delivery of vaccine.

Yet another object of the present invention is oral or nasal delivery of Tetanus, Botulinum, Diphtheria, and Pertussis Vaccine either alone or in combination thereof.

Another object of the present invention is to provide process for preparation of composition for the vaccine.

BRIEF SUMMARY OF THE INVENTION

Accordingly present invention provides a composition of neurotoxin associated proteins and vaccine.

Another embodiment of the present invention wherein the neurotoxin associated proteins (NAPs) is of botulinum neurotoxin.

Another embodiment of the present invention wherein the neurotoxin associated proteins (NAPs) are used as a delivery vehicle for tetanus vaccine delivery.

Another embodiment of the present invention wherein the vaccine selected from the group consisting of tetanus, diphtheria and pertussis alone or in combination thereof.

Another embodiment of the present invention wherein tetanus vaccine is non-toxic protein domain of TeNT.

Another embodiment of the present invention the non-toxic protein domain of TeNT is selected from heavy (H) chain or detoxified recombinant TeNT (DrTeNT) alone or in combination thereof.

Another embodiment of the present invention wherein the detoxified recombinant TeNT (DrTeNT) is selected from mutated light chain or native heavy chain or combination thereof.

Another embodiment of the present invention wherein vaccine is made of a fusion with DrTeNT or any of its derived fragments with diphtheria vaccine element.

Another embodiment of the present invention wherein vaccine DrTeNT is combined with pertussis vaccine element as a fusion protein.

Another embodiment of the present invention wherein vaccine DrTeNT combined with vaccine elements of diphtheria and pertussis vaccine elements as a fusion protein.

Further embodiment of the present invention is a process for the preparation of second generation tetanus toxoid vaccine, ie, tetanus heavy chain comprising steps of;
   a. Induction of E. coli culture $OD_{600}$=0.5 by adding 0.2 mM IPTG
   b. Growing culture for 14-16° C. at 14 to 20 hours
   c. the cell paste suspends in 25 mM phosphate buffer containing 200 mM sodium chloride
   d. add 1% of TRITON®-X-100 to the buffer
   e. Sonicate for a period of 3 minutes (3-5 sec on/off pulse) at 4° C. on cold beads.
   f. Centrifuge the culture for 60 to 90 minutes.
   g. Supernatant is collected; and
   h. Supernatant purified using Ni-NTA affinity column.
   i. Combine the pool which has less contaminated bands and concentrate the pool by using CENTRIPREP®-30.

Another embodiment of the present invention, the process, wherein the pH of buffer in the range of 7.2 to 8.0

Another embodiment of the present invention, the process. wherein the pH of buffer is preferably 7.4

Another embodiment of the present invention wherein, in process, rpm of centrifuge rotation is 8000-15000 rpm per hour for 45 to 90 minutes.

Another embodiment of the present invention wherein eluent is imidazole solution.

Yet another embodiment of the present invention wherein the concentration of imidazole solution is 10 mM, 50 mM, 100 mM, 200 mM and 500 mM.

Accordingly the present invention relates a process for preparation of third generation detoxified recombinant tetanus toxoid vaccine comprising steps of;
   a. pBN3 vector was used for cloning TeTx Light chain in a BL21(DE3) strain for expression of the plasmid.
   b. Two active sites mutation, E234A and E271A, was done which corresponds to E224 and E262 of BoNT/A active sites.
   c. HC portion of TeNT was fused to construct full length tetanus neurotoxin plasmid with two active sites mutation, E234A and E271A.
   d. Purified the large band at 150 kDa protein position using Ni-NTA affinity column.

Yet another embodiment of the present invention a process wherein strain used for expression of the plasmid E. coli BL21 (DE3).

Yet another embodiment of the present invention is a process wherein purified large band at 150 kDa protein is obtained as soluble and stable.

Accordingly present invention relates a process for the preparation of vaccine and NAPs composition comprises
   a. mixing equimolar ratio of vaccine and NAPs at pH 5.5 to 6.2
   b. Reacting at an ambient temperature for 2-3 hours
   c. 25 mM phosphate buffer of pH 5.8 containing 200 mM sodium chloride solution charged to step 2
   d. reacting above obtained reaction mixture with 10 mM imidazole solution
   e. The reaction mixture further loaded to G-100 column
   f. eluted the column to get the pure NAPs-vaccine composition.

Yet another embodiment of the present invention is a process wherein vaccine is selected from the group consisting of tetanus, diphtheria, pertussis alone or combination thereof.

Yet another embodiment of the present invention is a process, wherein temperature in range of 20-30° C.

Yet another embodiment of the present invention is a process where in preferred pH is 5.8.

Yet another embodiment of the present invention is a process wherein tetanus vaccine is a non-toxic protein domain of TeNT.

Yet another embodiment of the present invention is a process wherein tetanus vaccine is selected from heavy (H) chain or detoxified recombinant TeNT (DrTeNT) alone or in combination thereof.

Yet another embodiment of the present invention is a process wherein, detoxified recombinant TeNT is selected from mutated light chain or native heavy chain or combination thereof.

Yet another embodiment of the present invention is a process wherein NAPs is from botulinum neurotoxin.

Yet another embodiment of the present invention is a process wherein the NAPs are obtained from any serotype of *C. botulinum*.

Yet another embodiment of the present invention is a process wherein tetanus vaccine is linked to detoxified botulinum neurotoxin (DrBoNT).

Yet another embodiment of the present invention is a process wherein tetanus vaccine is linked to a fragment of detoxified botulinum neurotoxin.

Yet another embodiment of the present invention is a process wherein tetanus vaccine is linked to NAPs of botulinum neurotoxin.

Yet another embodiment of the present invention is the composition is used for the oral or nasal delivery of vaccine.

Yet another embodiment of the present invention is the vaccine is selected from the group consisting of tetanus, diphtheria or pertussis alone or in combination thereof.

Yet another embodiment of the present invention is the tetanus vaccine is non-toxic protein domain of TeNT.

Yet another embodiment of the present invention is the non toxic protein domain of TeNT is selected from heavy (H) chain or detoxified recombinant TeNT (DrTeNT) alone or in combination thereof.

Yet another embodiment of the present invention is the detoxified recombinant TeNT (DrTeNT) is selected from mutated light chain or native heavy chain or combination thereof.

Yet another embodiment of the present invention is the vaccine is made of a fusion with DrTeNT or any of its derived fragments with diphtheria vaccine element.

Yet another embodiment of the present invention is the DrTeNT is combined with pertussis vaccine element as a fusion protein.

The vaccine as claimed in claim 32, wherein DrTeNT is combined with vaccine elements of diphtheria and pertussis vaccine elements as a fusion protein.

DETAILED DESCRIPTION OF THE INVENTION

The present invention employs use of neurotoxin associated proteins (NAPs) of botulinum neurotoxin (BoNT) produced by *Clostridium botulinum* as a delivery vehicles of tetanus vaccine. BoNT is a food poison produced in the form of a complex with NAPs, which protect it from the low pH and proteases of the gastro-intestinal tract. In addition, NAPs are known to help in translocation of the BoNT across the mucosal layer of intestine as well as the nasal passage. Given the similarity of structure of BoNT and TeNT and their common mode of action, NAPs bind and protect and translocate a tetanus vaccine across the mucosal layer.

*Clostridium botulinum* produces seven serotypes of botulinum neurotoxins (A-G). It is basically made of two protein chains one is 100 kDa polypeptide heavy chain and another is 50 kDa polypeptide light chain bridged through disulphide link. Botulinum neurotoxins is synthesized in a complex form, in which neurotoxin is surrounded by several non-toxin proteins known as neurotoxin associated proteins (NAPs). NAPs have been shown to have two major roles in the intoxication process of botulism. The first role is the assistance of NAPs in the translocation of the BoNT across the intestinal mucosal layer. The second role is NAPs protect the BoNT against acidity and proteolytic attack of the enzymes of gastric juice. Therefore it becomes a perfect delivery system for vaccine. The TeNT, having over 35% sequence homology with BoNTs, and sharing much of the structural and functional features of BoNT, but is not a food poison due to the lack of NAPs. NAPs from one serotype of BoNT bind and protect another serotype of BoNT, thus these can also bind, protect and deliver vaccines, specially TeNT or TeNT vaccine due to sequence homology and common structural and functional domains. Therefore, the present invention uses BoNT's NAPs for oral and intranasal delivery of vaccines, specially tetanus vaccine.

Botulinum and tetanus neurotoxins have several common features including over 35% sequence homology, and antagonistic effects of heterologous protein fragments. Both the neurotoxins have similar secondary structural contents, and both have their 'catalytic domain' light chain on the C-terminal of their amino acid sequence. Tetanus is capable of causing botulism symptoms at high concentrations and blocks the release of acetylcholine from the presynaptic membranes just like the BoNT.

Similar mechanism of action for botulinum and tetanus neurotoxins at the molecular level occurs. Experimental studies reveal many similarities between the two neurotoxins including the membrane channel formation by the N-terminal fragments of their respective heavy chains and blockage of the neurotransmitter release from cultured cells and proteolytic activity against synaptobrevin-2. It is believed that there is enough common structural and functional similarity between BoNT and TeNT. The botulinum NAPs bind and protect TeNT similar to BoNT/A, providing basis for NAPs use an oral carrier of vaccine, specially tetanus vaccine.

BoNT is a food poison produced in the form of a complex with NAPs (see FIG. 1). NAPs protect BoNT from the low pH and proteases of the gastro-intestinal tract (Mahmut et al., 2002). NAPs are known to help translocate the BoNT across the mucosal layer of intestine as well as the nasal passage (Fujinaga et al., 2004). Given the similarity of structure of BoNT and TeNT and their common mode of action, Hn-33 is likely to bind and protect and translocate a tetanus vaccine across the mucosal layer (Mahmut et al., 2002).

Due to 35% sequence homology, and antagonistic effects of heterologous protein fragments, there is evidence for strong common structural features. Also, the ability of tetanus for causing botulism symptoms at high concentrations just like the BoNT it is likely that these proteins have a similar mechanism of action for botulinum and tetanus neurotoxins at the molecular level.

Experimental studies revealed many similarities between the two neurotoxins including the membrane channel formation by the N-terminal fragments of their respective heavy chains and blockage of the neurotransmitter release from cultured cells and proteolytic activity against synaptobrevin-2. Therefore there is enough common structural and functional similarity between BoNT and TeNT that NAPs of BoNT/A NAPs will bind and protect TeNT similar to BoNT/A, which provides basis for NAPs use an oral carrier of vaccines, especially tetanus vaccine.

The Tetanus toxoid vaccine, a second generation vaccine is prepared based on the non-toxic protein domain of TeNT, such as the heavy (H) chain for demonstrating its binding and delivery by NAPs.

Figure 2:
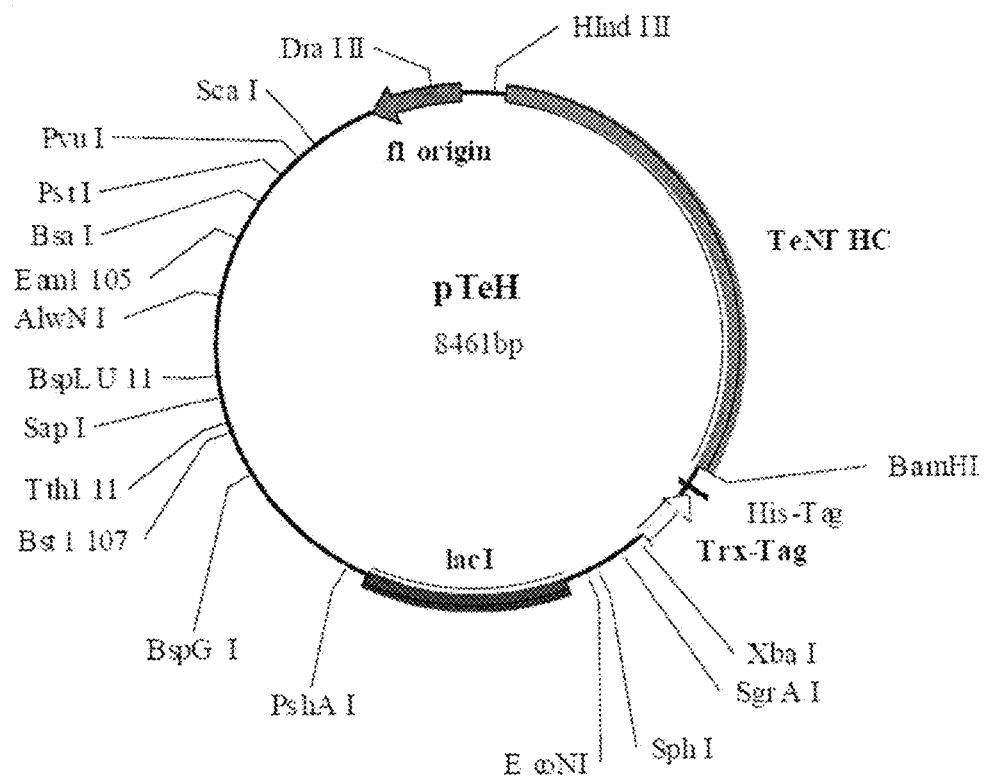
FIG. 2 shows a diagram illustrating pTeH plasmid, which is 8461 bp in length, comprising TeNT heavy chain, TeNT HC 2580 bp in length cloned in pET32a vector between BamHI and HindIII sites, fused with thioredoxin-tag (Trx-Tag) and His-tag at N-terminal.

The first steps include the preparation of a second generation tetanus vaccine based on the non-toxic heavy chain of the TeNT. FIG. 2 shows the schematic genomic map of pET32a, showing the location of TeNT heavy chain TeNT heavy chain plasmids were transferred to BL21(DE3) competent cells, and grown in the LB media. The *E. coli* culture was induced at $OD_{600}=0.5$ by adding 0.2 mM IPTG and after induction culture continually grew at 16° C. for about 16 hours.

Second step is the preparation of NAPs from type A *Clostridium botulinum*

Finally, demonstration of NAPs binding to the second generation tetanus vaccine.

Present invention also provides method of preparation of the clone of DrTeNT as the third generation tetanus vaccine.

The third generation tetanus vaccine is prepared from and/or detoxified recombinant TeNT (DrTeNT) is cloned in pET32a vector between BamHI and HindIII sites with the N-terminal his-tag.

We also demonstrate protection of vaccine by NAPs against low pH and gastric protease, and further demonstration of the oral and intranasal delivery of the tetanus vaccine in rabbits (FIG. 12) by evaluating protection against challenge with TeNT, and allows one to compare the results with those obtained by intramuscular injections. Next, in this preferred embodiment, one may develop primate model for testing the effectiveness of the oral and intranasal delivery of tetanus vaccine by NAPs as an initial step towards testing this needle free delivery system in humans.

Preparation of NAPs from Botulinum Neurotoxin

Botulinum neurotoxin and purification of NAPs is done as per known method in the art (Kukreja et al., Toxicon, 2009 (53) 616-624).

Preparation of Tetanus Toxoid Vaccine

In this preferred embodiment, the cell paste culture suspended in about 1 L, 25 mM phosphate buffer, pH 7.4, containing 200 mM sodium chloride and 1% of TRITON®-X-100 added in the buffer (called basic buffer). After sonication, the cell lysate was centrifuged at 12,000 rpm for about 1 hour by using Thermo Scientific® Sorvall® Legend® RT Centrifuge and FIBERLite® F15-8x50C rotor, and then the supernatant is poured into a clean tube. The extract is thus obtained and is loaded to the pre-equilibrated Ni-NTA column.

After loading to the Ni-NTA affinity column, 10 mM imidazole is added to the basic buffer as a washing step, then protein binding to the column is eluted step by step at 50 mM imidazole, 100 mM imidazole, 200 mM imidazole and 500 mM imidazole. Next, one should combine the pool which has less contaminated bands and concentrate the pool by using CENTRIPREP®-30. After concentration, measure the protein concentration by UV, then prepare to do further binding experiments with NAPs.

Figure 3:
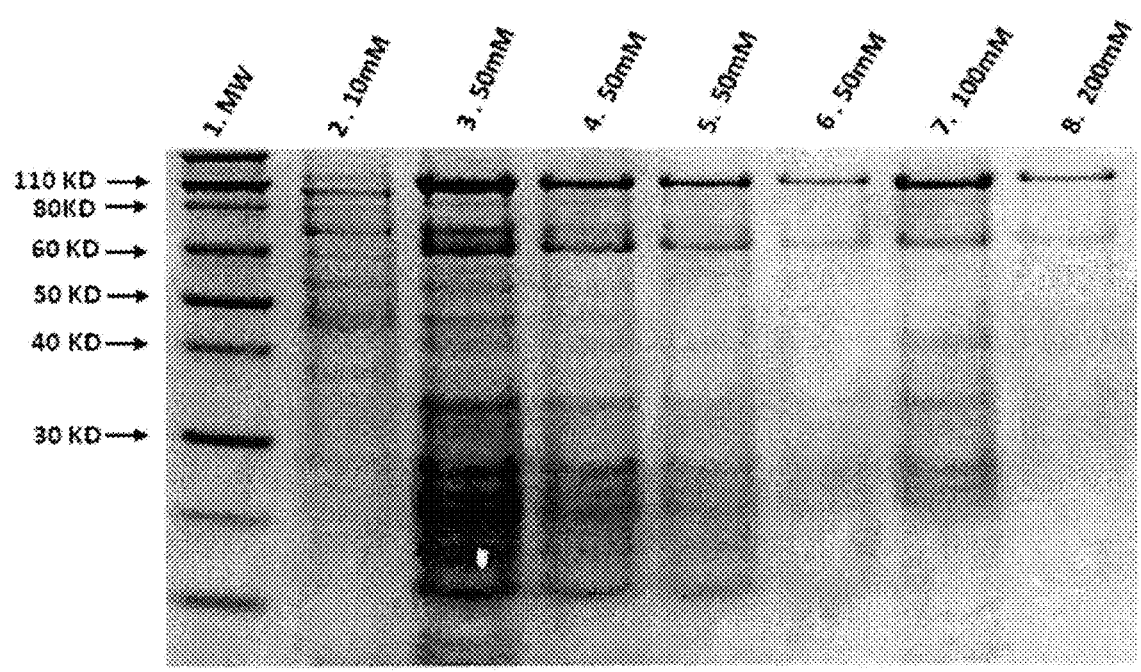
FIG. 3 shows the results of purification of recombinant TeNT heavy chain through $Ni^{2+}$-affinity column (Ni-NTA; Nickel-Nitrilotriacetic acid) chromatography.

Purification results of TeNT heavy chain obtained in this embodiment are shown in FIG. 3.

Preparation of Detoxified Recombinant TeNT

The detoxified recombinant TeNT (DrTeNT) was prepared by cloning the TeNT gene and mutating two active site glutamic amino acid residues, E234 and E271 each to alanine residues. Cloning of Dr TeNT involved three steps: (1) pBN3 vector was used for cloning TeTx Light chain. (2) Two active sites mutation, E234A and E271A, was done which corresponds to E224 and E262 of BoNT/A active sites. (3) HC portion of TeNT was fused to construct full length tetanus neurotoxin plasmid with two active sites mutation, E234A and E271A.

*E. coli* BL21 (DE3) was used for the protein expression vector. After induction there were a large band at 150 kDa position which was the size of full length recombinant tetanus neurotoxin. After Ni-NTA affinity column, about 5 mg/ml pure protein was obtained which was soluble and stable.

FIG. 3 shows the results of purification of recombinant TeNT heavy chain through $Ni^{2+}$-affinity column chromatography. Lane1 is MW standards. Lane 2 is Ni-NTA (Nickel-Nitrilotriacetic acid) affinity column washing with 10 mM imidazole added in the basic buffer. Lanes 3-6 are elution with 50 mM imidazole concentration. Lane 7 is elution with 100 mM Imidazole. Lane 8 is elution with 200 mM imidazole.

Preparation of NAPs-Tetanus Heavy Chain Composition

In another preferred embodiment, tetanus heavy chain has N-terminal his-tag which can bind to Ni-NTA affinity column, but NAPs which is purified from botulinum neurotoxin complex cannot bind to the Ni-NTA affinity column, so pull down assay is used for analysis to demonstrate if heavy chain would bind with NAPs. If Heavy chain has interaction with NAPs, both HC and NAPs would remain bound to NTA column and will be released together from Ni-NTA affinity column after eluting with imidazole.

Approximately equal molar ratio of tetanus heavy chain and NAPs are mixed together at pH 5.8. Binding reaction is carried out at room temperature for 2 hours. 25 mM phosphate buffer, pH 5.8, containing 200 mM NaCl is used for procedure of pull down assay. After reaction, the reaction mixture is diluted to a final imidazole concentration lower than 5 mM. The reaction mixture is loaded to the Ni-NTA affinity column, and 10 mM imidazole is added to the basic buffer to wash column at 20× bed volume, then the protein is eluted stepwise with 50 mM, 100 mM, 200 mM, 500 mM imidazole. The eluents are examined with SDS-PAGE to check the purity and intactness of the TeNT heavy chain, as illustrated in FIG. 3.

Tetanus heavy chain purified from different batches is used for the binding experiments. After HC and NAPs reaction at room temperature, reaction mixture is reloaded to the Ni-NTA affinity column, with 10 mM Imidazole added to the basic phosphate buffer for washing column. After then protein is eluted with 50 mM, 100 mM, 200 mM imidazole. From the gel, it was observed that Tetanus heavy chain and NAPs were eluted together at 50 mM imidazole concentration (FIG. 4).

Figure 4:
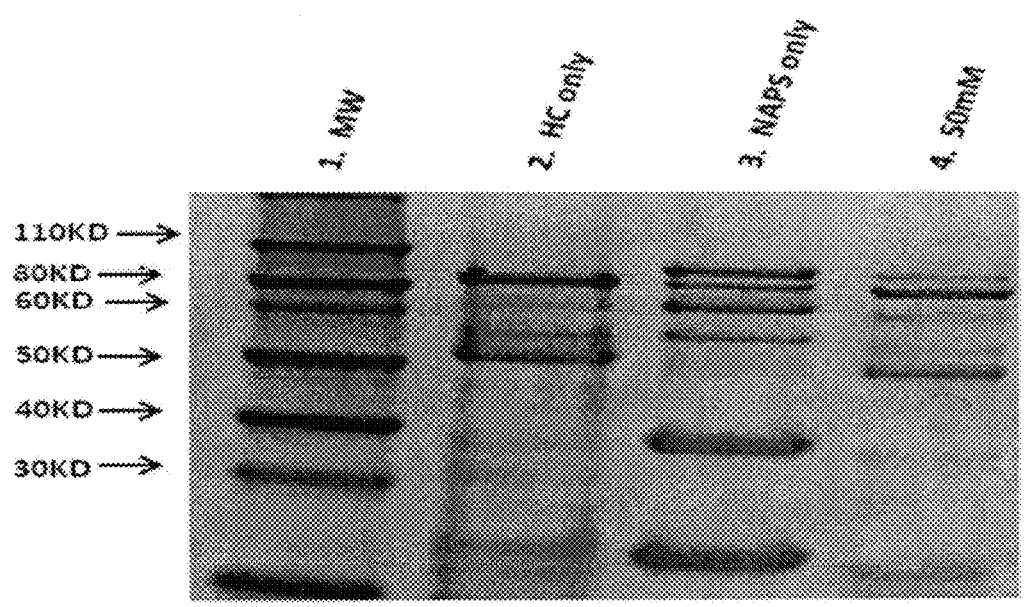
FIG. 4 shows the results of binding of recombinant tetanus heavy chain (HC) preparation with NAPs as analyzed on $Ni^{2+}$-affinity column chromatography.

FIG. 4 shows binding of recombinant tetanus heavy chain (HC) preparation with NAPs as analyzed on $Ni^{2+}$-affinity column chromatography. Lane 1 is MW. Lane 2 is intact heavy chain protein. Lane 3 is intact NAPs. Lane 4 is elution from Ni-NTA affinity column with imidazole 50 mM after loading HC and NAPs reaction mixture to Ni-NTA affinity column, Lane 4 showed HC and NAPs came together at 50 mM imidazole concentration.

NAPs results shown in FIG. 4, lane 4, demonstrating that the NAPs successfully bound to the tetanus heavy chain. This observation would suggest that the tetanus heavy chain could be carried through the digestive system when administered orally in combination with NAPs. The NAPs are also expected to deliver the tetanus heavy chain or whole tetanus toxin across the intestinal mucosal layer.

Binding between tetanus heavy chain and NAPs is therefore demonstrated. Prepared clone of detoxified recombinant TeNT or DrTeNT which is full length TeNT with only two active site amino acid residues mutated (FIG. 5 and FIG. 6) has been achieved. DrTeNT has been successfully cloned in a pBN3 vector between E.coRI and PstI sites with C-terminal his-tag. The schematic diagram of new vector construct, named pDrT vector, is shown in FIG. 7.

FIG. 5 shows nucleotide sequence of DrTeNT (3951 bp, including stop codon) which encodes for the full length double mutant tetanus gene. The start codon is enclosed in a green box, which is the same start for TeNT light chain; the double mutation sites are enclosed in orange boxes, GAA (Glu) to GCA (ALA) mutation; the heavy chain start codon (TCA) is enclosed in black box; and the stop codon is enclosed in a red box following the six His tag.

FIG. 6 shows the amino acid sequence alignment of DrTeNT, reference (data from wildtype genomic DNA), and CN3911 from Genebank. The two red boxes show that two active sites which got mutated in DrTeNT from wild type. The black boxes show that amino acid sequence variation from GeneBank *C. tetani* strain.

Figure 7:
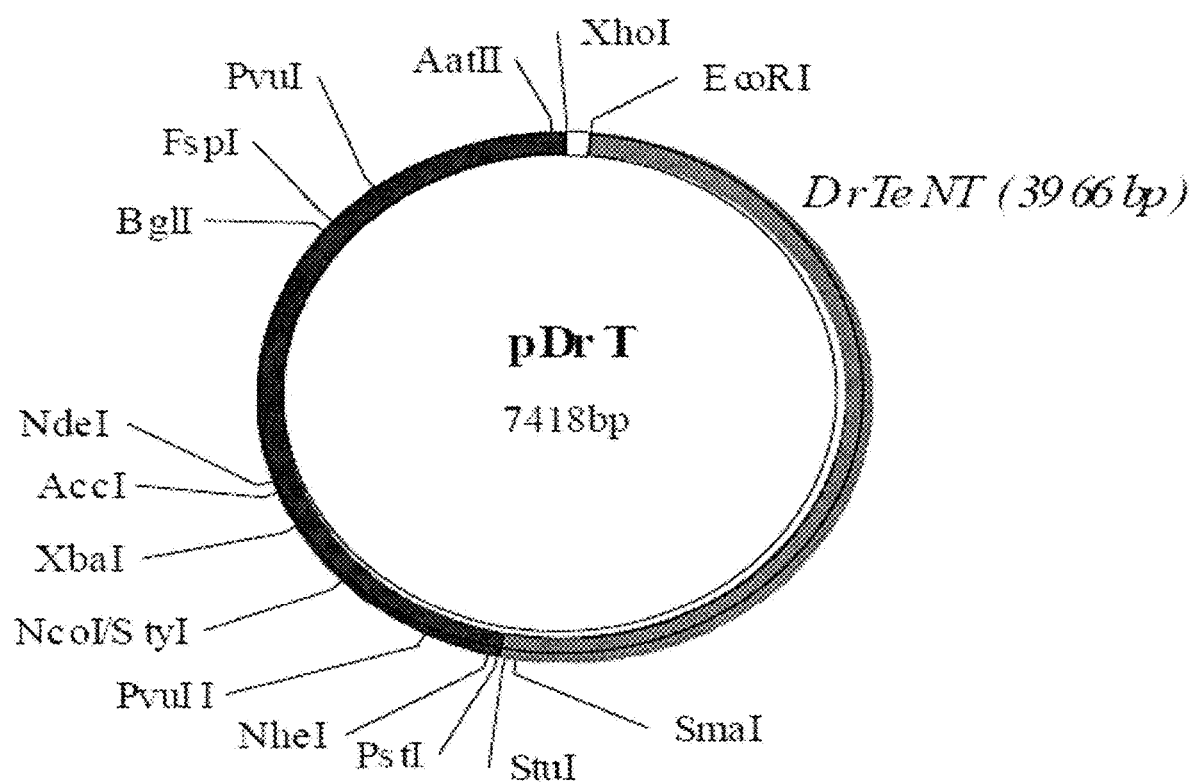
FIG. 7 shows a schematic representation of pDrT vector map containing DrTeNT gene, shown in grey color (3966 bp include 6-His tag).

FIG. 7 shows a schematic representation of pDrT vector map containing DrTeNT gene (3966 bp include 6-His tag). DrTeNT was cloned in pBN3 vector (3452 bp), between E.coRI and PstI sites. The new construction of pDrT vector is 7418 bp in length.

Figure 8A:
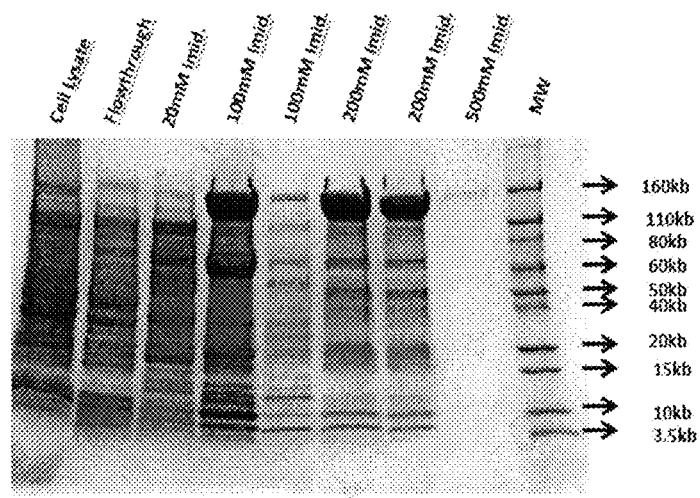
FIG. 8A-8B shows Dr TeNT protein purification process and the end product. 8A shows Dr TeNT was purified by using NTA column. Dr TeNT has his-tag at C-terminal and the molecular weight of Dr TeNT is about 150 kDa, and the protein eluted from column around 100 mm-200 mM Imidazole. 8B shows the purified Dr TeNT.
Figure 8B:
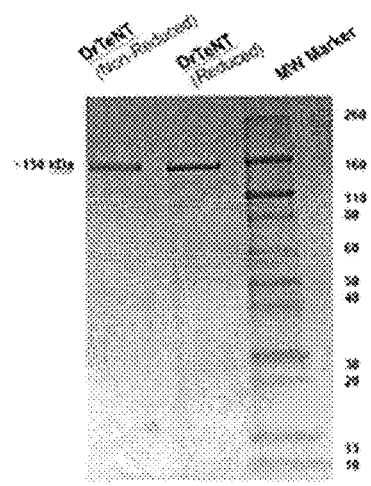

Expression of DrTeNT gene in *E. coli* has been achieved and better than 99% pure DrTeNT is purified on a Ni-NTA affinity column (FIG. 8).

Figure 9:
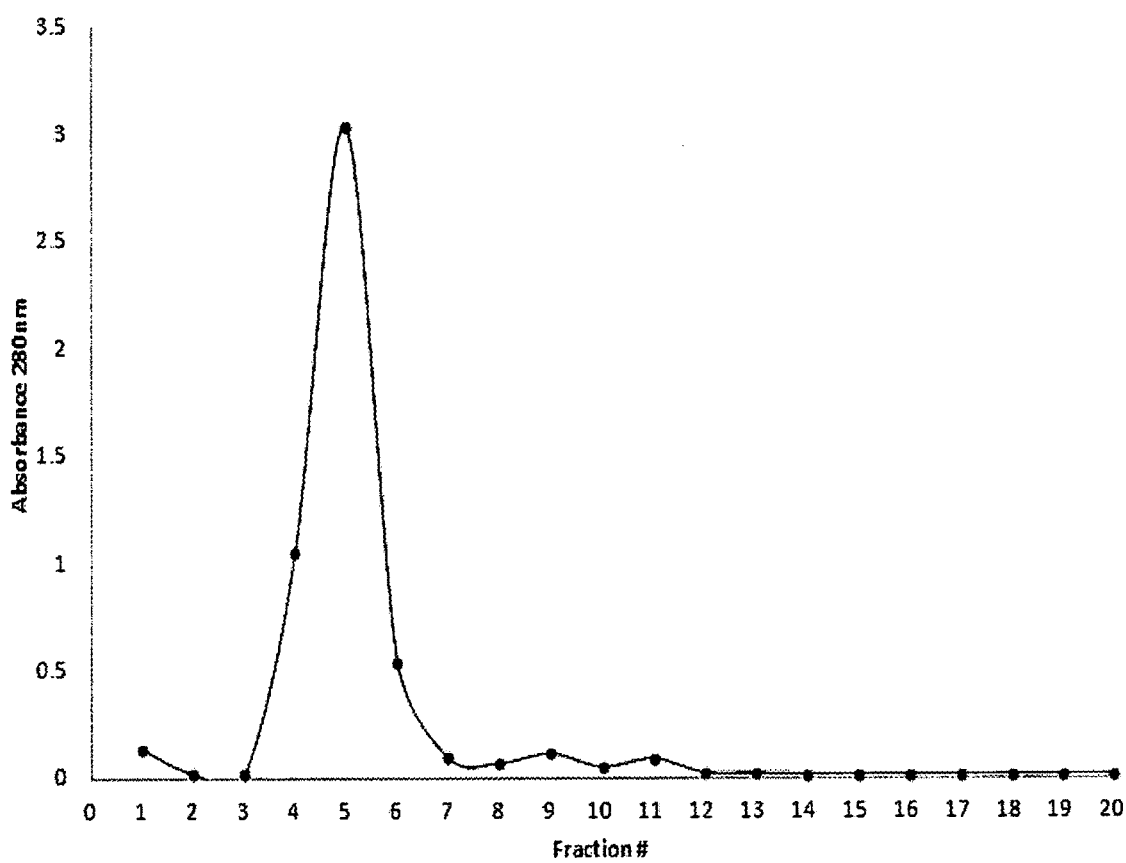
FIG. 9. Binding of NAPs and DrTeNT is demonstrated using a G-100 gel filtration column chromatography performed in 50 mM sodium phosphate buffer, pH 5.8, containing 200 mM NaCl, showing a single peak elution of the mixture containing all the NAPs and DrTeNT.
Figure 10:
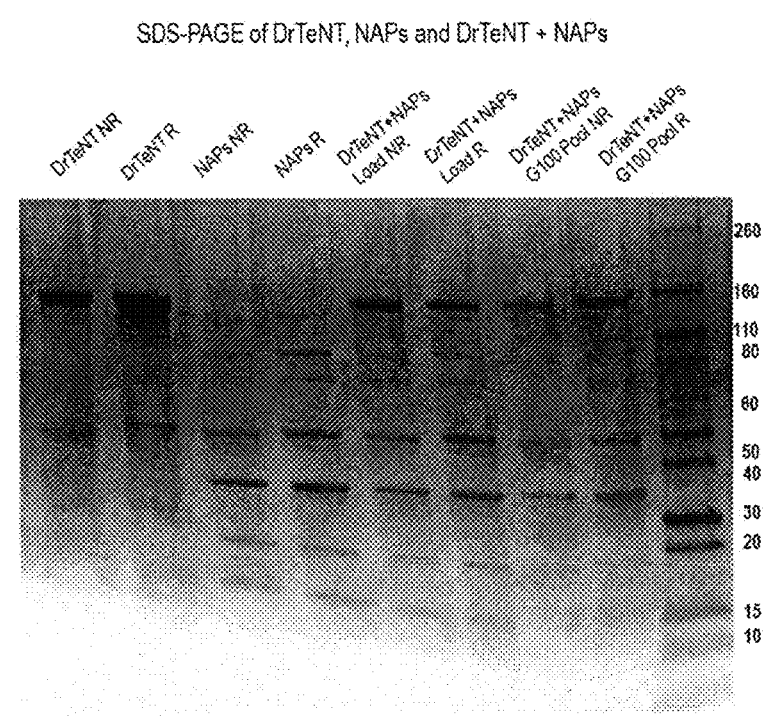
Figure 11:
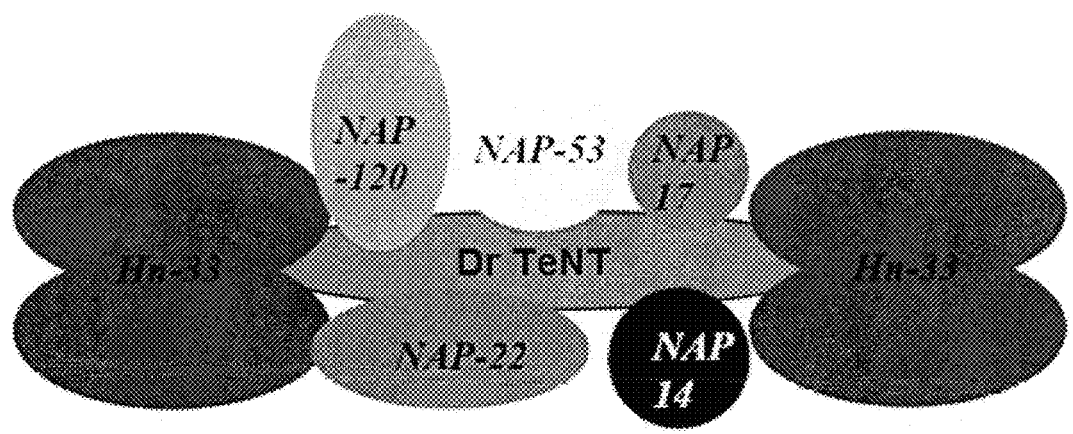
FIG. 11. Schematic model of the DrTeNT-NAPs complex.

Binding of NAPs and DrTeNT is demonstrated using a G-100 gel filtration column chromatography performed in 50 mM sodium phosphate buffer, pH 5.8, containing 200 mM NaCl, showing a single peak elution of the mixture containing all the NAPs and DrTeNT (FIG. 9). Binding of NAPs and DrTeNT is confirmed by SDS-PAGE gel (FIG. 10). A model of the DrTeNT and NAPs complex is shown in FIG. 11.

In another preferred embodiment the binding of the NAPs to tetanus heavy chain or DrTeNT is done using high-performance liquid chromatography (HPLC). In this preferred embodiment both NAPs and HC (used as a control) run separately when passed through the size exclusion column. After mixing them together at low pH conditions for binding with each other, and the mixture will appear as a single elution band.

In another preferred embodiment the binding of the NAPs to tetanus heavy chain is done using enzyme-linked immunosorbent assay (ELISA). In this preferred embodiment the tetanus heavy chain is coated on the 96 well plate at various different concentration Incubation of NAPs labeled with Horseradish Peroxidase (HRP) will show concentration dependent binding as monitored by colorimetric method by adding HRP substrate.

In another preferred embodiment the binding of the NAPs to tetanus heavy chain or DrTeNT is done using a BIA-CORE® surface plasmon resonance. In this preferred embodiment binding is evaluated on a gold chip.

In another preferred embodiment the binding of the NAPs to tetanus heavy chain or DrTeNT is done using isothermal calorimetry. In this preferred embodiment titration of a given concentration of NAPs with varying concentrations of tetanus vaccine candidate will show changes in heat evolved, thus allowing calculation of binding constant.

In another preferred embodiment the binding of the NAPs to tetanus heavy chain or DrTeNT is done using Fluorescence anisotropy. In this preferred embodiment the tetanus vaccine candidate can be labelled with a fluorescent probe, and titrated with the NAPs by monitoring fluorescence anisotropy.

In another preferred embodiment the binding of the NAPs to tetanus heavy chain, DrTeNT, or any other fragment thereof is demonstrated with x-ray crystallography.

In another preferred embodiment the binding of the NAPs to tetanus heavy chain or DrTeNT is demonstrated with electron microscopy.

In another preferred embodiment the binding of the NAPs to tetanus heavy chain, DrTeNT, or any other fragment thereof is demonstrated with NMR spectroscopy.

In another preferred embodiment the binding of the NAPs to tetanus heavy chain, DrTeNT, or any other fragment thereof is demonstrated with molecular dynamic simulations.

In another preferred embodiment the binding of the NAPs to tetanus heavy chain, DrTeNT, or any other fragment thereof is demonstrated with circular dichroism spectroscopy.

In another preferred embodiment the binding of the NAPs to tetanus heavy chain, DrTeNT, or any other fragment thereof is demonstrated with FTIR spectroscopy.

Figure 12:
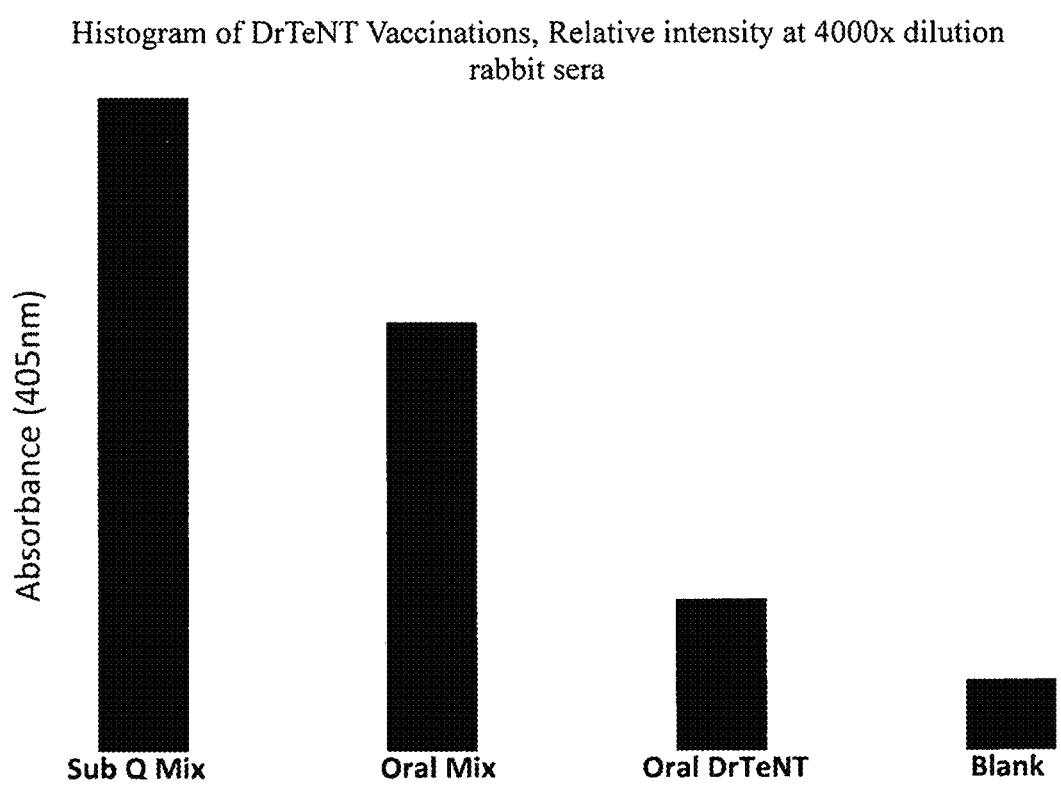
FIG. 12. The immune response of the proposed construct with oral delivery as well as subcutaneous delivery.

Evaluation of the Oral Delivery of Tetanus Vaccine
The effectiveness of inducing an immune response with oral delivery as well as subcutaneous delivery is shown in FIG. 12. The first bar Sub Q Mix is subcutaneous mixture of NAPs with DrTeNT, next bar is same material via oral root and then oral DrTeNT alone. Although subcutaneous is more effective to illicit a response it seem that via oral mixture of both articles are more effective than the DrTeNT alone.

In another preferred embodiment neurotoxin associated protein from botulinum neurotoxin complex used as a delivery system for a tetanus vaccine.

In another preferred embodiment a neurotoxin associated protein from botulinum neurotoxin used as a delivery system for a tetanus vaccine.

In another preferred embodiment the tetanus heavy chain is used.

In another preferred embodiment the tetanus heavy chain linked to a botulinum toxin fragment is used.

In another preferred embodiment DrTeNT linked to DrBoNT is used.

In another embodiment a neurotoxin associated protein from botulinum neurotoxin complex is used as delivery system to botulinum vaccine.

In another embodiment neurotoxin associated proteins from botulinum neurotoxin complex is used as delivery system to botulinum vaccine.

In another embodiment, DrBoNT or any other fragment thereof is used as a vaccine.

In another preferred embodiment the neurotoxin associated protein is obtained from *Clostridium botulinum*.

In another preferred embodiment the neurotoxin associated protein is obtained from recombinant protein expression system.

In another preferred embodiment the neurotoxin associated protein is obtained from *Clostridium botulinum* bind to tetanus heavy chain.

In another preferred embodiment the detoxified recombinant form of whole tetanus neurotoxin (DrTeNT) containing mutated light chain and native heavy chain is used as vaccine alone for oral and intranasal delivery.

In another preferred embodiment the detoxified form of whole tetanus neurotoxin containing mutated light chain and native heavy chain is used as vaccine in combination with the neurotoxin associated protein for oral and intranasal delivery.

In another preferred embodiment the DrTeNT is combined with diphtheria vaccine element as a fusion protein.

In another preferred embodiment the DrTeNT is combined with pertussis vaccine element as a fusion protein.

In another preferred embodiment the DrTeNT is combined with vaccine elements of diphtheria and pertussis vaccine elements as a fusion protein.

In another preferred embodiment the group of neurotoxin associated proteins (NAPs) is used as a delivery vehicle for tetanus vaccine delivery.

In another preferred embodiment the tetanus vaccine is heavy chain of tetanus.

In another preferred embodiment the tetanus vaccine is light chain of tetanus.

In another preferred embodiment the tetanus vaccine is any fragment of tetanus.

In another preferred embodiment the vaccine is made of a fusion with DrTeNT or any of its derived fragments with diphtheria vaccine element.

In another preferred embodiment the vaccine is made of a fusion with DrTeNT or any of its derived fragments with pertussis vaccine element.

In another preferred embodiment the vaccine is made of a fusion with DrTeNT or any of its derived fragments with pertussis and diphtheria vaccine elements.

In another preferred embodiment the drug is created by combining DrTeNT or any of its fragments with any other drug candidate.

Applicant has described applicant's preferred embodiments of this invention, however it will be understood that the broadest scope of this invention includes modifications such as use of other equipment and laboratory procedures. Such scope is limited only by the claims as read in connection with the specification. Other advantages of the present invention will be apparent to those skilled in the art from the descriptions and the claims.

Advantage of the Invention

Present invention gives a novel composition of neurotoxin associated protein and vaccine.
The neurotoxin associated protein helps in oral or nasal delivery of vaccine, especially tetanus vaccine with or without diphtheria and pertussis.
Further, present invention gives a novel process for the preparation of second and third generation of vaccine.
Present invention also provides a novel process for the preparation of composition of neurotoxin associated protein and vaccine for oral delivery or nasal delivery.
Present invention also provides a method for evaluation of the efficiency of the oral delivery of vaccine.

What is claimed is:

1. A process for the preparation of a vaccine and neurotoxin associated proteins (NAPs) composition, comprising:
    mixing an equimolar ratio of the vaccine and neurotoxin associated proteins (NAPs) into a mixture that is maintained at a pH of from 5.5 to 6.2,
        wherein the vaccine comprises a detoxified recombinant protein(s) derived from one or more proteins associated with an infectious disease selected from the group consisting of tetanus, diphtheria, pertussis alone or in combination thereof;
        wherein the neurotoxin associated proteins (NAPs) are derived from *Clostridium botulinum* or botulinum neurotoxin, and the NAPs become chemically or recombinantly linked or otherwise associated to the vaccine during the mixing;
    maintaining the mixture at the pH in the range of from 5.5 to 6.2 using 25 mM phosphate buffer at a pH 5.8 containing 200 mM sodium chloride solution;
    reacting the mixture with at least 10 mM imidazole solution at an ambient temperature for from 2 to 3 hours;
    loading the mixture to a Nickel-Nitrilotriacetic acid (Ni-NTA) affinity column; and
    eluting the column to get a pure vaccine and neurotoxin associated proteins (NAPs) composition.

2. The process of claim 1, wherein the vaccine comprises a detoxified recombinant tetanus neurotoxin (DrTeNT).

3. The process of claim 1, wherein the imidazole concentration is at least 50 mM.

4. The process of claim 1, wherein the temperature is in the range of 20-30° C.

5. The process of claim 1, wherein the mixture is maintained at a pH of 5.8.

6. The process of claim 1, wherein the vaccine is a tetanus vaccine that is chemically or recombinantly linked or otherwise associated to a detoxified botulinum neurotoxin (DrBoNT) or any other vehicle, or carrier molecule.

7. The process of claim 1, wherein the vaccine is a tetanus vaccine that is chemically or recombinantly linked or otherwise associated to a fragment of detoxified botulinum neurotoxin (DrBoNT).

8. The process of claim 1, wherein the vaccine is a tetanus vaccine that is chemically or recombinantly linked or otherwise associated to the neurotoxin associated proteins (NAPs) of *Clostridium botulinum* or botulinum neurotoxin during the mixing of the equimolar ratio of the tetanus vaccine and the neurotoxin associated proteins (NAPs).

9. The process of claim 1, wherein the vaccine is a tetanus vaccine that is chemically or recombinantly linked or otherwise associated to neurotoxin associated proteins (NAPs) of any other serotypes and subtypes B to G of *Clostridium botulinum* or botulinum neurotoxin during the mixing of the equimolar ratio of the tetanus vaccine and the neurotoxin associated proteins (NAPs).

10. The process of claim 9, wherein the vaccine comprises a detoxified recombinant tetanus neurotoxin (DrTeNT) that is combined with a pertussis vaccine element as a fusion protein.

11. The process of claim 9, wherein the vaccine comprises a detoxified recombinant tetanus neurotoxin (DrTeNT) that is combined with a vaccine elements of diphtheria and pertussis vaccine elements as a fusion protein.

12. The process of claim 9, wherein the tetanus vaccine comprises detoxified recombinant tetanus neurotoxin (DrTeNT) formulated to be administered orally, subcutaneously or intraperitoneally, either alone or in combination with a vaccine elements of diphtheria and pertussis vaccine as a fusion protein.

13. The process of claim 9, wherein the tetanus vaccine comprises a detoxified tetanus neurotoxin (DrTeNT), or one or more of its fragments that is conjugated covalently or non-covalently with a therapeutic drug comprising a therapeutic small molecule or a therapeutic biomolecules.

\* \* \* \* \*

SEQUENCE LISTING

<160> NUMBER OF SEQ ID NOS: 3

<210> SEQ ID NO 1
<211> LENGTH: 1315
<212> TYPE: PRT
<213> ORGANISM: Clostridium tetani
<220> FEATURE:
<221> NAME/KEY: misc_feature
<222> LOCATION: (1193)..(1193)
<223> OTHER INFORMATION: Xaa can be any naturally occurring amino acid

<400> SEQUENCE: 1

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350
```

-continued

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
        500                 505                 510

Ile Leu Asp Tyr Asn Leu Gln Ser Lys Ile Thr Leu Pro Asn Asp Arg
    515                 520                 525

Thr Thr Pro Val Thr Lys Gly Ile Pro Tyr Ala Pro Glu Tyr Lys Ser
530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

```
Glu Gln Ile Ala Asp Glu Ile Asn Asn Leu Lys Asn Lys Leu Glu Glu
770             775                 780
Lys Ala Asn Lys Ala Met Ile Asn Ile Asn Ile Phe Met Arg Glu Ser
785             790                 795                 800
Ser Arg Ser Phe Leu Val Asn Gln Met Ile Asn Glu Ala Lys Lys Gln
            805                 810                 815
Leu Leu Glu Phe Asp Thr Gln Ser Lys Asn Ile Leu Met Gln Tyr Ile
            820                 825                 830
Lys Ala Asn Ser Lys Phe Ile Gly Ile Thr Glu Leu Lys Lys Leu Glu
            835                 840                 845
Ser Lys Ile Asn Lys Val Phe Ser Thr Pro Ile Pro Phe Ser Tyr Ser
850             855                 860
Lys Asn Leu Asp Cys Trp Val Asp Asn Glu Glu Asp Ile Asp Val Ile
865             870                 875                 880
Leu Lys Lys Ser Thr Ile Leu Asn Leu Asp Ile Asn Asn Asp Ile Ile
                885                 890                 895
Ser Asp Ile Ser Gly Phe Asn Ser Ser Val Ile Thr Tyr Pro Asp Ala
            900                 905                 910
Gln Leu Val Pro Gly Ile Asn Gly Lys Ala Ile His Leu Val Asn Asn
            915                 920                 925
Glu Ser Ser Glu Val Ile Val His Lys Ala Met Asp Ile Glu Tyr Asn
930             935                 940
Asp Met Phe Asn Asn Phe Thr Val Ser Phe Trp Leu Arg Val Pro Lys
945             950                 955                 960
Val Ser Ala Ser His Leu Glu Gln Tyr Gly Thr Asn Glu Tyr Ser Ile
            965                 970                 975
Ile Ser Ser Met Lys Lys Tyr Ser Leu Ser Ile Gly Ser Gly Trp Ser
            980                 985                 990
Val Ser Leu Lys Gly Asn Asn Leu Ile Trp Thr Leu Lys Asp Ser Ala
            995             1000                1005
Gly Glu Val Arg Gln Ile Thr Phe Arg Asp Leu Ser Asp Lys Phe
        1010                1015                1020
Asn Ala Tyr Leu Ala Asn Lys Trp Val Phe Ile Thr Ile Thr Asn
        1025                1030                1035
Asp Arg Leu Ser Ser Ala Asn Leu Tyr Ile Asn Gly Val Leu Met
        1040                1045                1050
Gly Ser Ala Glu Ile Thr Gly Leu Gly Ala Ile Arg Glu Asp Asn
        1055                1060                1065
Asn Ile Thr Leu Lys Leu Asp Arg Cys Asn Asn Asn Gln Tyr
        1070                1075                1080
Val Ser Ile Asp Lys Phe Arg Ile Phe Cys Lys Ala Leu Asn Pro
        1085                1090                1095
Lys Glu Ile Glu Lys Leu Tyr Thr Ser Tyr Leu Ser Ile Thr Phe
        1100                1105                1110
Leu Arg Asp Phe Trp Gly Asn Pro Leu Arg Tyr Asp Thr Glu Tyr
        1115                1120                1125
Tyr Leu Ile Pro Val Ala Ser Ser Ser Lys Asp Val Gln Leu Lys
        1130                1135                1140
Asn Ile Thr Asp Tyr Met Tyr Leu Thr Asn Ala Pro Ser Tyr Thr
        1145                1150                1155
Asn Gly Lys Leu Asn Ile Tyr Tyr Arg Arg Leu Tyr Asn Gly Leu
        1160                1165                1170
Lys Phe Ile Ile Lys Arg Tyr Thr Pro Asn Asn Glu Ile Asp Ser
```

-continued

```
             1175                1180                1185

Phe Val Lys Ser Xaa Asp Phe Ile Lys Leu Tyr Val Ser Tyr Asn
         1190                1195                1200

Asn Asn Glu His Ile Val Gly Tyr Pro Lys Asp Gly Asn Ala Phe
         1205                1210                1215

Asn Asn Leu Asp Arg Ile Leu Arg Val Gly Tyr Asn Ala Pro Gly
         1220                1225                1230

Ile Pro Leu Tyr Lys Lys Met Glu Ala Val Lys Leu Arg Asp Leu
         1235                1240                1245

Lys Thr Tyr Ser Val Gln Leu Lys Leu Tyr Asp Lys Asn Ala
         1250                1255                1260

Ser Leu Gly Leu Val Gly Thr His Asn Gly Gln Ile Gly Asn Asp
         1265                1270                1275

Pro Asn Arg Asp Ile Leu Ile Ala Ser Asn Trp Tyr Phe Asn His
         1280                1285                1290

Leu Lys Asp Lys Ile Leu Gly Cys Asp Trp Tyr Phe Val Pro Thr
         1295                1300                1305

Asp Glu Gly Trp Thr Asn Asp
         1310                1315

<210> SEQ ID NO 2
<211> LENGTH: 1377
<212> TYPE: PRT
<213> ORGANISM: Clostridium tetani
<220> FEATURE:
<221> NAME/KEY: misc_feature
<222> LOCATION: (1195)..(1195)
<223> OTHER INFORMATION: Xaa can be any naturally occurring amino acid

<400> SEQUENCE: 2

Ile Gly Met Pro Ile Thr Ile Asn Asn Phe Arg Tyr Ser Asp Pro Val
1               5                   10                  15

Asn Asn Asp Thr Ile Ile Met Met Glu Pro Pro Tyr Cys Lys Gly Leu
            20                  25                  30

Asp Ile Tyr Tyr Lys Ala Phe Lys Ile Thr Asp Arg Ile Trp Ile Val
        35                  40                  45

Pro Glu Arg Tyr Glu Phe Gly Thr Lys Pro Glu Asp Phe Asn Pro Pro
    50                  55                  60

Ser Ser Leu Ile Glu Gly Ala Ser Glu Tyr Tyr Asp Pro Asn Tyr Leu
65                  70                  75                  80

Arg Thr Asp Ser Asp Lys Asp Arg Phe Leu Gln Thr Met Val Lys Leu
                85                  90                  95

Phe Asn Arg Ile Lys Asn Asn Val Ala Gly Glu Ala Leu Leu Asn Lys
            100                 105                 110

Ile Ile Asn Ala Ile Pro Tyr Leu Gly Asn Ser Tyr Ser Leu Leu Asp
        115                 120                 125

Lys Phe Asp Thr Asn Ser Asn Ser Val Ser Phe Asn Leu Leu Glu Gln
    130                 135                 140

Asp Pro Ser Gly Ala Thr Thr Lys Ser Ala Met Leu Thr Asn Leu Ile
145                 150                 155                 160

Ile Phe Gly Pro Gly Pro Val Leu Asn Lys Asn Glu Val Arg Gly Ile
                165                 170                 175

Val Leu Arg Val Asp Asn Lys Asn Tyr Phe Pro Cys Arg Asp Gly Phe
            180                 185                 190

Gly Ser Ile Met Gln Met Ala Phe Cys Pro Glu Tyr Val Pro Thr Phe
        195                 200                 205
```

```
Asp Asn Val Ile Glu Asn Ile Thr Ser Leu Thr Ile Gly Lys Ser Lys
    210                 215                 220
Tyr Phe Gln Asp Pro Ala Leu Leu Leu Met His Ala Leu Ile His Val
225                 230                 235                 240
Leu His Gly Leu Tyr Gly Met Gln Val Ser Ser His Glu Ile Ile Pro
                    245                 250                 255
Ser Lys Gln Glu Ile Tyr Met Gln His Thr Tyr Pro Ile Ser Ala Glu
                260                 265                 270
Ala Leu Phe Thr Phe Gly Gly Gln Asp Ala Asn Leu Ile Ser Ile Asp
            275                 280                 285
Ile Lys Asn Asp Leu Tyr Glu Lys Thr Leu Asn Asp Tyr Lys Ala Ile
    290                 295                 300
Ala Asn Lys Leu Ser Gln Val Thr Ser Cys Asn Asp Pro Asn Ile Asp
305                 310                 315                 320
Ile Asp Ser Tyr Lys Gln Ile Tyr Gln Gln Lys Tyr Gln Phe Asp Lys
                325                 330                 335
Asp Ser Asn Gly Gln Tyr Ile Val Asn Glu Asp Lys Phe Gln Ile Leu
            340                 345                 350
Tyr Asn Ser Ile Met Tyr Gly Phe Thr Glu Ile Glu Leu Gly Lys Lys
    355                 360                 365
Phe Asn Ile Lys Thr Arg Leu Ser Tyr Phe Ser Met Asn His Asp Pro
370                 375                 380
Val Lys Ile Pro Asn Leu Leu Asp Asp Thr Ile Tyr Asn Asp Thr Glu
385                 390                 395                 400
Gly Phe Asn Ile Glu Ser Lys Asp Leu Lys Ser Glu Tyr Lys Gly Gln
                405                 410                 415
Asn Met Arg Val Asn Thr Asn Ala Phe Arg Asn Val Asp Gly Ser Gly
            420                 425                 430
Leu Val Ser Lys Leu Ile Gly Leu Cys Lys Lys Ile Ile Pro Pro Thr
    435                 440                 445
Asn Ile Arg Glu Asn Leu Tyr Asn Arg Thr Ala Ser Leu Thr Asp Leu
450                 455                 460
Gly Gly Glu Leu Cys Ile Lys Ile Lys Asn Glu Asp Leu Thr Phe Ile
465                 470                 475                 480
Ala Glu Lys Asn Ser Phe Ser Glu Glu Pro Phe Gln Asp Glu Ile Val
                485                 490                 495
Ser Tyr Asn Thr Lys Asn Lys Pro Leu Asn Phe Asn Tyr Ser Leu Asp
            500                 505                 510
Lys Ile Ile Leu Asp Tyr Asn Leu Gln Ser Lys Ile Thr Leu Pro Asn
    515                 520                 525
Asp Arg Thr Thr Pro Val Thr Lys Gly Ile Pro Tyr Ala Pro Glu Tyr
530                 535                 540
Lys Ser Asn Ala Ala Ser Thr Ile Glu Ile His Asn Ile Asp Asp Asn
545                 550                 555                 560
Thr Ile Tyr Gln Tyr Leu Tyr Ala Gln Lys Ser Pro Thr Thr Leu Gln
                565                 570                 575
Arg Ile Thr Met Thr Asn Ser Val Asp Asp Ala Leu Ile Asn Ser Thr
            580                 585                 590
Lys Ile Tyr Ser Tyr Phe Pro Ser Val Ile Ser Lys Val Asn Gln Gly
    595                 600                 605
Ala Gln Gly Ile Leu Phe Leu Gln Trp Val Arg Asp Ile Ile Asp Asp
    610                 615                 620
```

-continued

Phe Thr Asn Glu Ser Ser Gln Lys Thr Thr Ile Asp Lys Ile Ser Asp
625                 630                 635                 640

Val Ser Thr Ile Val Pro Tyr Ile Gly Pro Ala Leu Asn Ile Val Lys
            645                 650                 655

Gln Gly Tyr Glu Gly Asn Phe Ile Gly Ala Leu Glu Thr Thr Gly Val
            660                 665                 670

Val Leu Leu Leu Glu Tyr Ile Pro Glu Ile Thr Leu Pro Val Ile Ala
            675                 680                 685

Ala Leu Ser Ile Ala Glu Ser Ser Thr Gln Lys Glu Lys Ile Ile Lys
            690                 695                 700

Thr Ile Asp Asn Phe Leu Glu Lys Arg Tyr Glu Lys Trp Ile Glu Val
705                 710                 715                 720

Tyr Lys Leu Val Lys Ala Lys Trp Leu Gly Thr Val Asn Thr Gln Phe
            725                 730                 735

Gln Lys Arg Ser Tyr Gln Met Tyr Arg Ser Leu Glu Tyr Gln Val Asp
            740                 745                 750

Ala Ile Lys Lys Ile Ile Asp Tyr Glu Tyr Lys Ile Tyr Ser Gly Pro
            755                 760                 765

Asp Lys Glu Gln Ile Ala Asp Glu Ile Asn Asn Leu Lys Asn Lys Leu
            770                 775                 780

Glu Glu Lys Ala Asn Lys Ala Met Ile Asn Ile Asn Ile Phe Met Arg
785                 790                 795                 800

Glu Ser Ser Arg Ser Phe Leu Val Asn Gln Met Ile Asn Glu Ala Lys
            805                 810                 815

Lys Gln Leu Leu Glu Phe Asp Thr Gln Ser Lys Asn Ile Leu Met Gln
            820                 825                 830

Tyr Ile Lys Ala Asn Ser Lys Phe Ile Gly Ile Thr Glu Leu Lys Lys
            835                 840                 845

Leu Glu Ser Lys Ile Asn Lys Val Phe Ser Thr Pro Ile Pro Phe Ser
850                 855                 860

Tyr Ser Lys Asn Leu Asp Cys Trp Val Asp Asn Glu Glu Asp Ile Asp
865                 870                 875                 880

Val Ile Leu Lys Lys Ser Thr Ile Leu Asn Leu Asp Ile Asn Asn Asp
            885                 890                 895

Ile Ile Ser Asp Ile Ser Gly Phe Asn Ser Ser Val Ile Thr Tyr Pro
            900                 905                 910

Asp Ala Gln Leu Val Pro Gly Ile Asn Gly Lys Ala Ile His Leu Val
            915                 920                 925

Asn Asn Glu Ser Ser Glu Val Ile Val His Lys Ala Met Asp Ile Glu
            930                 935                 940

Tyr Asn Asp Met Phe Asn Asn Phe Thr Val Ser Phe Trp Leu Arg Val
945                 950                 955                 960

Pro Lys Val Ser Ala Ser His Leu Glu Gln Tyr Gly Thr Asn Glu Tyr
            965                 970                 975

Ser Ile Ile Ser Ser Met Lys Lys Tyr Ser Leu Ser Ile Gly Ser Gly
            980                 985                 990

Trp Ser Val Ser Leu Lys Gly Asn Asn Leu Ile Trp Thr Leu Lys Asp
            995                 1000                1005

Ser Ala Gly Glu Val Arg Gln Ile Thr Phe Arg Asp Leu Ser Asp
    1010                1015                1020

Lys Phe Asn Ala Tyr Leu Ala Asn Lys Trp Val Phe Ile Thr Ile
    1025                1030                1035

Thr Asn Asp Arg Leu Ser Ser Ala Asn Leu Tyr Ile Asn Gly Val

```
               1040                1045                1050
Leu Met Gly Ser Ala Glu Ile Thr Gly Leu Gly Ala Ile Arg Glu
       1055                1060                1065

Asp Asn Asn Ile Thr Leu Lys Leu Asp Arg Cys Asn Asn Asn Asn
       1070                1075                1080

Gln Tyr Val Ser Ile Asp Lys Phe Arg Ile Phe Cys Lys Ala Leu
       1085                1090                1095

Asn Pro Lys Glu Ile Glu Lys Leu Tyr Thr Ser Tyr Leu Ser Ile
       1100                1105                1110

Thr Phe Leu Arg Asp Phe Trp Gly Asn Pro Leu Arg Tyr Asp Thr
       1115                1120                1125

Glu Tyr Tyr Leu Ile Pro Val Ala Ser Ser Lys Asp Val Gln
       1130                1135                1140

Leu Lys Asn Ile Thr Asp Tyr Met Tyr Leu Thr Asn Ala Pro Ser
       1145                1150                1155

Tyr Thr Asn Gly Lys Leu Asn Ile Tyr Tyr Arg Arg Leu Tyr Asn
       1160                1165                1170

Gly Leu Lys Phe Ile Ile Lys Arg Tyr Thr Pro Asn Asn Glu Ile
       1175                1180                1185

Asp Ser Phe Val Lys Ser Xaa Asp Phe Ile Lys Leu Tyr Val Ser
       1190                1195                1200

Tyr Asn Asn Asn Glu His Ile Val Gly Tyr Pro Lys Asp Gly Asn
       1205                1210                1215

Ala Phe Asn Asn Leu Asp Arg Ile Leu Arg Val Gly Tyr Asn Ala
       1220                1225                1230

Pro Gly Ile Pro Leu Tyr Lys Lys Met Glu Ala Val Lys Leu Arg
       1235                1240                1245

Asp Leu Lys Thr Tyr Ser Val Gln Leu Lys Leu Tyr Asp Asp Lys
       1250                1255                1260

Asn Ala Ser Leu Gly Leu Val Gly Thr His Asn Gly Gln Ile Gly
       1265                1270                1275

Asn Asp Pro Asn Arg Asp Ile Leu Ile Ala Ser Asn Trp Tyr Phe
       1280                1285                1290

Asn His Leu Lys Asp Lys Ile Leu Gly Cys Asp Trp Tyr Phe Val
       1295                1300                1305

Pro Thr Asp Glu Gly Trp Thr Asn Asp His His His His His His
       1310                1315                1320

Gly Leu Gln Pro Ser Leu Ile Ser Ala Trp Thr Pro Val Asp Arg
       1325                1330                1335

Ser Ser Asn Asp Leu Arg Thr Pro Ser Gly Phe Val Gln Asn Ala
       1340                1345                1350

Arg Leu Pro Pro Gly Val Phe Tyr Trp Glu Ser Lys Leu Ala Trp
       1355                1360                1365

Arg Asp Phe Gln Glu Leu Arg Lys Leu
       1370                1375

<210> SEQ ID NO 3
<211> LENGTH: 3948
<212> TYPE: DNA
<213> ORGANISM: Clostridium tetani

<400> SEQUENCE: 3
atgccaataa ccataaataa ttttagatat agtgatcctg ttaataatga tacaattatt      60
atgatggagc caccatactg taagggtcta gatatctatt ataaggcttt caaaataaca     120
```

```
gatcgtattt ggatagtgcc ggaaaggtat gaatttggga caaaacctga agattttaac      180
ccaccatctt cattaataga aggtgcatct gagtattacg atccaaatta tttaaggact      240
gattctgata aagatagatt tttacaaacc atggtaaaac tgtttaacag aattaaaaac      300
aatgtagcag gtgaagcctt attagataag ataataaatg ccatacctta ccttggaaat      360
tcatattcct tactagacaa gtttgataca aactctaatt cagtatcttt taatttatta      420
gaacaagacc ccagtggagc aactacaaaa tcagcaatgc tgacaaattt aataatattt      480
ggacctgggc ctgttttaaa taaaaatgag gttagaggta ttgtattgag ggtagataat      540
aaaaattact tcccatgtag agatggtttt ggctcaataa tgcaaatggc attttgccca      600
gaatatgtac ctacctttga taatgtaata gaaaatatta cgtcactcac tattggcaaa      660
agcaaatatt ttcaagatcc agcattacta ttaatgcacg aacttataca tgtactacat      720
ggtttatacg gaatgcaggt atcaagccat gaaattattc catccaaaca gaaatttat       780 atgcagcata catatccaat aagtgctgaa gaactattca cttttggcgg acaggatgct      840
aatcttataa gtattgatat aaaaaacgat ttatatgaaa aactttaaa tgattataaa       900 gctatagcta acaaacttag tcaagtcact agctgcaatg atcccaacat tgatattgat      960
agctacaaac aaatatatca acaaaaatat caattcgata agatagcaa tggacaatat      1020 attgtaaatg aggataaatt tcagatacta tataatagca taatgtatgg ttttacagag     1080
attgaattgg gaaaaaaatt taatataaaa actagacttt cttattttag tatgaatcat     1140
gaccctgtaa aaattccaaa tttattagat gatacaattt acaatgatac agaaggattt     1200
aatatagaaa gcaaagatct gaaatctgaa tataaaggac aaaatatgag ggtaaataca     1260
aatgctttta gaaatgttga tggatcaggc ctagtttcaa aacttattgg cttatgtaaa     1320
aaaattatac caccaacaaa tataagagaa aatttatata atagaactgc atcattaaca     1380
gatttaggag gagaattatg tataaaaatt aaaaatgaag atttaacttt tatagctgaa     1440
aaaaatagct tttcagaaga accatttcaa gatgaaatag ttagttataa tacaaaaaat     1500
aaaccattaa attttaatta ttcgctagat aaaattattg tagattataa tctacaaagt     1560
aaaattacat tacctaatga taggacaacc ccagttacaa aaggaattcc atatgctcca     1620
gaatataaaa gtaatgctgc aagtacaata gaaatacata atattgatga caatacaata     1680
tatcaatatt tgtatgctca aaaatctcct acaactctac aaagaataac tatgactaat     1740
tctgttgatg acgcattaat aaattccacc aaaatatatt catattttcc atctgtaatc     1800
agtaaagtta accaaggtgc acaaggaatt ttattcttac agtgggtgag agatataatt     1860
gatgatttta ccaatgaatc ttcacaaaaa actactattg ataaaatttc agatgtatcc     1920
actattgttc cttatatagg acccgcatta aacattgtaa acaaggcta tgagggaaac     1980 tttataggcg ctttagaaac taccggagtg gttttattat tagaatatat tccagaaatt     2040
actttaccag taattgcagc tttatctata gcagaaagta gcacacaaaa agaaagata     2100 ataaaaacaa tagataactt tttagaaaaa agatatgaaa aatggattga agtatataaa     2160
ctagtaaaag caaatggtt aggcacagtt aatacgcaat tccaaaaaag aagttatcaa     2220
atgtatagat cttttagaata tcaagtagat gcaataaaaa aaataataga ctatgaatat     2280
aaaatatatt caggacctga taaggaacaa attgccgacg aaattaataa tctgaaaaac     2340
aaacttgaag aaaaggctaa taaagcaatg ataaacataa atatatttat gagggaaagt     2400
tctagatcat ttttagttaa tcaaatgatt aacgaagcta aaaagcagtt attagagttt     2460
```

-continued

```
gatactcaaa gcaaaaatat tttaatgcag tatataaaag caaattctaa atttataggt    2520
ataactgaac taaaaaaatt agaatcaaaa ataaacaaag tttttttcaac accaattcca    2580 ttttcttatt ctaaaaatct ggattgttgg gttgataatg aagaagatat agatgttata    2640
ttaaaaaaga gtacaatttt aaatttagat attaataatg atattatatc agatatatct    2700
gggtttaatt catctgtaat aacatatcca gatgctcaat tggtgcccgg aataaatggc    2760
aaagcaatac atttagtaaa caatgaatct tctgaagtta tagtgcataa agctatggat    2820
attgaatata atgatatgtt taataatttt accgttagct tttggttgag ggttcctaaa    2880
gtatctgcta gtcatttaga acaatatggc acaaatgagt attcaataat tagctctatg    2940
aaaaaacata gtctatcaat aggatctggt tggagtgtat cacttaaagg taataactta    3000
atatggactt taaaagattc cgcgggagaa gttagacaaa taactttttag ggatttacct   3060 gataaattta atgcttattt agcaaataaa tgggtttttta taactattac taatgataga   3120
ttatcttctg ctaatttgta tataaatgga gtacttatgg gaagtgcaga aattactggt    3180
ttaggagcta ttagagagga taataatata acattaaaac tagatagatg taataataat    3240
aatcaatacg tttctattga taaatttagg atattttgca aagcattaaa tccaaaagag    3300
attgaaaaat tatacacaag ttatttatct ataacctttt taagagactt ctggggaaac    3360
cctttacgat atgatacaga atattattta ataccagtag cttctagttc taaagatgtt    3420
caattgaaaa atataacaga ttatatgtat ttgacaaatg cgccatcgta tactaacgga    3480
aaattgaata tatattatag aaggttatat aatggactaa aatttattat aaaaagatat    3540
acacctaata atgaaataga ttcttttgtt aaatcaggtg attttattaa attatatgta   3600
tcatataaca ataatgagca cattgtaggt tatccgaaag atggaaatgc ctttaataat   3660
cttgataaga ttctaagagt aggttataat gccccaggta tccctctttta taaaaaaatg   3720 gaagcagtaa aattgcgtga tttaaaaacc tattctgtac aacttaaatt atatgatgat   3780
aaaaatgcat ctttaggact agtaggtacc cataatggtc aaataggcaa cgatccaaat   3840
agggatatat taattgcaag caactggtac tttaatcatt taaaagataa aattttagga   3900
tgtgattggt actttgtacc tacagatgaa ggatggacaa atgattaa                 3948
```